(12) United States Patent
Smith et al.

(10) Patent No.: US 11,331,337 B2
(45) Date of Patent: May 17, 2022

(54) HEPARIN AND HEPARAN SULPHATE OLIGOSACCHARIDES

(71) Applicant: Agency for Science, Technology and Research, Singapore (SG)

(72) Inventors: Raymond Alexander Alfred Smith, Singapore (SG); Simon McKenzie Cool, Singapore (SG); Victor Nurcombe, Singapore (SG); Sadasivam Murali, Tamil Nadu (IN)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 16/770,721

(22) PCT Filed: Dec. 11, 2018

(86) PCT No.: PCT/SG2018/050602
§ 371 (c)(1),
(2) Date: Jun. 8, 2020

(87) PCT Pub. No.: WO2019/117807
PCT Pub. Date: Jun. 20, 2019

(65) Prior Publication Data
US 2021/0161945 A1 Jun. 3, 2021

(30) Foreign Application Priority Data

Dec. 11, 2017 (SG) .......................... 10201710287Y

(51) Int. Cl.
*A61K 31/727* (2006.01)
(52) U.S. Cl.
CPC .................................. *A61K 31/727* (2013.01)
(58) Field of Classification Search
None
See application file for complete search history.

(56) References Cited

U.S. PATENT DOCUMENTS

2013/0045249 A1  2/2013  Cool et al.

FOREIGN PATENT DOCUMENTS

| WO | WO-93/19096 A1 | 9/1993 |
| WO | WO-2005/107772 A1 | 11/2005 |
| WO | WO-2006/045832 A1 | 5/2006 |
| WO | WO-2010/029278 A2 | 3/2010 |
| WO | WO-2010/030244 A1 | 3/2010 |
| WO | WO-2019/117807 A1 | 6/2019 |

OTHER PUBLICATIONS

Iduron, Selectively Desulphated Heparin Oligosaccharides, https://web.archive.org/web/20170922213109/http://iduron.co.uk/product/selectively-desulphated-heparin-oligosaccharides, accessed from the Wayback Machine internet archive, Sep. 22, 2017. (Year: 2017).*
Cole, C. et al., Synthetic Heparan Sulfate Oligosaccharides Inhibit Endothelial Cell Functions Essential for Angiogenesis, PLOS One, e11644, 5(7):1-15 (2010).
Iduron, Heparin Oligosaccharides and Desulphated Heparin Oligosaccharides, whole document (2017), <https://web.archive.org/web/20170922213004/https://iduron.co.uk/product/heparin-oligosaccharides; for the purpose of establishing publication date of this citation>. Retrieved on Jan. 31, 2019.
International Search Report for PCT/SG2018/050602, 7 pages (dated Apr. 3, 2019).
Ratanavaraporn, J. and Tabata, Y., Enhanced osteogenic activity of bone morphogenetic protein-2 by 2-O-desulfated heparin, Acta Biomaterialia, 8:173-182 (2012).
Seto, S. et al., Effect of Selective Heparin Desulfation on Preservation of Bone MorphogeneticProtein-2 Bioactivity after Thermal Stress, Bioconjugate Chem, 26:286-293 (2015).
Smith, R. et al., Minimum structural requirements for BMP-2-binding of heparin oligosaccharides, Biomaterials, 184:41-55 (2018).
Smith, R. et al., Retention of the Structure and Function of Heparan Sulfate Biomaterials After Gamma Irradiation, Tissue Engineering: Part A, 24(9-10):729-739 (2018).
Zhao, S. et al., Heparan Sulfate 6-O-Sulfotransferase 3 Is Involved in Bone Marrow.
Mesenchymal Stromal Cell Osteogenic Differentiation, Biochemistry (Moscow), 80(3):379-389 (2015).

* cited by examiner

*Primary Examiner* — Layla D Berry
(74) *Attorney, Agent, or Firm* — Choate, Hall & Stewart LLP; Kristen C. Buteau; Nicholas J. Pace

(57) ABSTRACT

Isolated heparin or heparan sulphate oligosaccharide fragments having a chain length of at least 10 saccharides and no more than 50 saccharides, which are capable of binding BMP2, are disclosed. Also disclosed is the use of the same heparin or heparan sulphate oligosaccharide fragments in kits and pharmaceutical compositions, and the use of the same heparan sulphate oligosaccharide fragments in the repair and/or regeneration of connective tissue and bones, and the treatment of wounds.

26 Claims, 16 Drawing Sheets

Specification includes a Sequence Listing.

| | HS3 <dp12 | HS3 >dp12<dp18 | HS3 >dp18<dp36 | HS3 >dp36 | HS3 full length |
|---|---|---|---|---|---|
| ΔUA-GlcNAc | 44.23 | 32.13 | 21.54 | 17.40 | 31.27 |
| ΔUA-GlcNS | 29.62 | 33.75 | 25.51 | 18.41 | 22.05 |
| ΔUA-GlcNAc,6S | 10.58 | 15.13 | 16.48 | 14.48 | 11.79 |
| ΔUA,2S-GlcNAc | 9.87 | 3.49 | 3.34 | 3.12 | 2.07 |
| ΔUA-GlcNS,6S | 0.00 | 3.30 | 8.96 | 12.97 | 9.67 |
| ΔUA,2S-GlcNS | 5.69 | 9.28 | 8.91 | 8.16 | 5.75 |
| ΔUA,2S-GlcNAc,6S | 0.00 | 0.00 | 0.00 | 0.00 | 0.00 |
| ΔUA,2S-GlcNS,6S | 0.00 | 2.92 | 15.26 | 25.47 | 17.40 |

|  | HS3 >dp36 | Heparin dp12 |
|---|---|---|
| ΔUA-GlcNAc | 17.40 | 3.92 |
| ΔUA-GlcNS | 18.41 | 1.65 |
| ΔUA-GlcNAc,6S | 14.48 | 2.88 |
| ΔUA,2S-GlcNAc | 3.12 | 0.00 |
| ΔUA-GlcNS,6S | 12.97 | 6.03 |
| ΔUA,2S-GlcNS | 8.16 | 5.13 |
| ΔUA,2S-GlcNAc,6S | 0.00 | 1.37 |
| ΔUA,2S-GlcNS,6S | 25.47 | 79.02 |

SEQUENCE LISTING

```
<160> NUMBER OF SEQ ID NOS: 2

<210> SEQ ID NO 1
<211> LENGTH: 18
<212> TYPE: PRT
<213> ORGANISM: Artificial Sequence
<220> FEATURE:
<223> OTHER INFORMATION: Heparin binding domain of BMP2

<400> SEQUENCE: 1

Gln Ala Lys His Lys Gln Arg Lys Arg Leu Lys Ser Ser Cys Lys Arg
1               5                   10                  15

His Pro

<210> SEQ ID NO 2
<211> LENGTH: 17
<212> TYPE: PRT
<213> ORGANISM: Artificial Sequence
<220> FEATURE:
<223> OTHER INFORMATION: Heparin binding domain of BMP2

<400> SEQUENCE: 2

Gln Ala Lys His Lys Gln Arg Lys Arg Leu Lys Ser Ser Cys Lys Arg
1               5                   10                  15

His
```

HEPARIN AND HEPARAN SULPHATE OLIGOSACCHARIDES

FIELD OF THE INVENTION

The present invention relates to heparin and heparan sulphate oligosaccharides, including heparin-type or heparan sulphate-type oligosaccharides of defined chain length and particularly, although not exclusively, to such oligosaccharides that bind BMP2.

BACKGROUND

Bone morphogenetic proteins (BMPs) are numbers of the transforming growth factor-β (TGF-β) superfamily that play crucial roles in various processes including mesoderm formation, neural patterning, skeletal development and limb formation (1, 2). More than 15 members of BMPs have been identified, and they play important roles in tissue repair and re-modeling processes after injuries (3-7). In animal models, several recombinant BMPs were reported to induce ectopic bone formation and enhance healing of critical-sized segmental bone defects. Clinical studies have shown that use of recombinant human BMPs is a safe and effective alternative to autologous bone grafting. Recombinant BMP2 and BMP-7 are approved for human use in spinal fusion and recalcitrant long-bone non-unions, respectively (4-7).

At the cellular level BMP signaling is initiated by binding two types of specific transmembrane serine/threonine kinase receptors namely type I (BMPR-I) and type II (BMPR-II) receptors (8). It has been shown that, BMP2 signaling results from binding to preaggregated receptor complexes rather than free receptors in the cell membrane (9). After ligand binding, the type I receptors are activated by the ligand bound II receptors. The activated type I receptor then phosphorylates members of the Smad family of intracellular proteins—Smad 1, Smad 5, and Smad 8—which in turn assemble into heteromeric complexes with Smad 4 that translocate into the nucleus to regulate transcription of target genes (10-12).

It is reported that, the in vivo and in vitro biological activities of BMPs were positively and negatively regulated by a large number of extracellular and cell surface sulphated polysaccharides such as heparin and heparan sulphate (HS) (8,13-20). BMP2 converts the differentiation pathway of C2C12 myoblasts into that of osteoblast lineage and heparin enhances BMP2 induced osteoblast differentiation in C2C12 myoblasts in vitro (20-22). As with other proteins, it is believed that specific size, and sulphated residues in the heparin/heparan sulphate chains bind to BMP2 and thereby modulate receptor-mediated signaling of these molecules.

Over the years, hundreds of HS-binding proteins have been identified, but how HS interacts with these proteins and affects their stability, concentration, conformation and activity is a fundamental question in biology. Several studies have demonstrated that the binding of growth factors to HS and thus giving rise to mitogenic activity happens only when specific structural features are present within the HS chain (23). Such features include sulphation at specific positions within a disaccharide; 6-O sulphated N-sulphate glucosamine and 2-O sulphated iduronic acid residues are particularly important, and minimum binding sequences are generally at least 5-6 disaccharides in length (24-26). The precise structures of HS that are involved in these interactions have remained elusive. Information on minimal binding sequences on HS is vital to understanding the rules of HS-protein interaction and design of HS mimics that can target proteins in human diseases. The minimal length and structural features of heparin/HS motifs have been identified in only a few cases (27-30). The first well studied example for the minimal length of the HS motif required for ligand binding and activity was the heparin-derived pentasaccharide were sufficient to interact with antithrombin III to inhibit clotting factors thrombin (IIa) and factor Xa (28-30). However, heparin-derived tetrasaccharide were sufficient to interact with fibroblast growth factor-2 (FGF-2), but oligosaccharides of degree of polymerization (dp) 10-12 are required for optimizing the proliferative activity of FGF-2. However, the structural sequence required for antithrombin III binding, where the most characteristic feature is the unusual 3-O sulphate group on a 6-O sulphate N-sulphoglucosamine residue (31). Furthermore, the structural characterization of a HS pattern that could bind FGF-2 has illustrated the importance of continuous stretches of the disulphide disaccharide N-sulphoglucosamine-iduronate 2-O sulphate for highest binding ability (32). These examples clearly demonstrated that the minimal oligosaccharide length units and specific structural features of HS pattern required for either binding or biological activity are not strictly related.

In this context, the characterization of the minimal HS unit and specific sulphate group of HS that binds BMP2 is of importance in an attempt to clarify the molecular mechanism that underline the requirement of HS in the regulation of BMP2 activity. However, HS is extremely heterogeneous in sequence and size and the source is limited. Heparin is similar in structure to the sulphated regions of HS. Therefore, in this study we examine the relationship between minimum length and specific sulphate group of heparin-derived oligosaccharides, which is required for binding to BMP2 and their capability to enhance BMP2 induced osteoblast differentiation on C2C12 myoblasts.

Previously, we identified and isolated an heparan sulphate that binds BMP2 with high affinity and showed that this HS has activity in the repair/regeneration of bone. Our work is reported in WO2010/030244 A1 and U.S. Pat. No. 9,498, 494.

SUMMARY OF THE INVENTION

In one aspect of the present invention an isolated heparin or heparan sulphate oligosaccharide is provided, the isolated heparin or heparan sulphate oligosaccharide having a chain length of at least 6 saccharides and no more than 50 saccharides.

Other aspects and embodiments are described in the appended claims.

In some embodiments the oligosaccharide has a chain length of one of: at least 8, at least 10, or at least 12 saccharides.

In some preferred embodiments the oligosaccharide comprises or consists of a chain length of 8, 10 or 12 saccharides.

In some embodiments the oligosaccharide has a chain length of no more than one of:49, 48, 47, 46, 45, 44, 43, 42, 41, 40, 39, 38, 37, 36, 35, 34, 33, 32, 32, 30, 29, 28, 27, 26, 25, 24, 23, 22, 21, 20, 19, 18, 17, 16, 15, 14, 13, 12, 11 or 10 saccharides.

In some embodiments the oligosaccharide has a chain length of one of 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 saccharides.

In some embodiments the oligosaccharide is N-sulphated. This may comprise N-sulphation of N-acetyl-D-glucosamine (GlcNAc) residues in the heparin or heparan sulphate oligosaccharide chain. Preferably at least 80% of N-acetyl-D-glucosamine (GlcNAc) residues in the isolated heparin or heparan sulphate are N-sulphated. In some embodiments this may be one of at least 85%, 90%, 95%, 96%, 97%, 98%, 99% or 100%.

In some embodiments the oligosaccharide is 6-O sulphated (O-sulphation at C6 of N-sulphoglucosamine (GlcNS) residues). Preferably at least 80% of N-sulphoglucosamine (GlcNS) residues in the heparin or heparan sulphate oligosaccharide chain are 6-O-sulphated. In some embodiments this may be one of at least 85%, 90%, 95%, 96%, 97%, 98%, 99% or 100%.

Although the oligosaccharide may be 2-O sulphated (O-sulphation at C2 of IdoA and GlcA) to a varying degree, in some embodiments the isolated heparin or heparan sulphate is 2-O de-sulphated.

In some embodiments the oligosaccharide binds BMP2 protein, optionally with a $K_D$ of less than one of: 100 μM, 50 μM, 10 μM, 1 μM, 100 nM, 50 nM, 10 nM or 1 nM.

Preparations or compositions comprising the isolated heparin or heparan sulphate are provided.

In one aspect of the present invention a pharmaceutical composition or medicament is provided comprising the isolated heparin or heparan sulphate in accordance with the aspects described above. The pharmaceutical composition or medicament may further comprise a pharmaceutically acceptable carrier, adjuvant or diluent.

In another aspect of the present invention a composition comprising the isolated heparin or heparan sulphate according to any one of the aspects above and BMP2 protein is provided.

In one aspect of the present invention the isolated heparin or heparan sulphate is provided for use in a method of treatment.

In a related aspect of the present invention the use of the isolated heparin or heparan sulphate in the manufacture of a medicament for use in a method of medical treatment is provided.

In another aspect of the present invention a method of treatment is provided, the method comprising the step of administering the isolated heparin or heparan sulphate to a subject in need of treatment thereof.

In aspects of the invention concerning a method of medical treatment the method of treatment may comprise a method of wound healing in vivo, the repair and/or regeneration of connective tissue, the repair and/or regeneration of bone and/or the repair and/or regeneration of bone in a mammal or a human. In some preferred embodiments the method of treatment comprises the repair and/or regeneration of a broken bone. In some embodiments the method of treatment may comprise simultaneous or sequential administration of BMP2 protein.

In some embodiment a method of treating a bone fracture in a patient is provided, the method comprising administration of a therapeutically effective amount of the isolated heparin or heparan sulphate to the patient. In some embodiments the method comprises administering the isolated heparin or heparan sulphate to the tissue surrounding the fracture. In some embodiments the method comprises injection of the isolated heparin or heparan sulphate to the tissue surrounding the fracture. In such methods the isolated heparin or heparan sulphate may be formulated as a pharmaceutical composition or medicament comprising the isolated heparin or heparan sulphate and a pharmaceutically acceptable carrier, adjuvant or diluent.

In some embodiments the method may further comprise administering BMP2 protein to the patient. In such methods the isolated heparin or heparan sulphate and BMP2 protein may be formulated as a pharmaceutical composition comprising the isolated heparin or heparan sulphate and BMP2 protein and a pharmaceutically acceptable carrier, adjuvant or diluent.

In a further aspect of the present invention a biocompatible implant or prosthesis comprising a biomaterial and the isolated heparin or heparan sulphate is provided. In some embodiments the implant or prosthesis is coated with the isolated heparin or heparan sulphate. In some embodiments the implant or prosthesis is impregnated with the isolated heparin or heparan sulphate.

In another aspect of the present invention a method of forming a biocompatible implant or prosthesis is provided, the method comprising the step of coating or impregnating a biomaterial with the isolated heparin or heparan sulphate. In some embodiments the method further comprises coating or impregnating the biomaterial with BMP2 protein.

In some embodiments a method of treating a bone fracture in a patient is provided, the method comprising surgically implanting a biocompatible implant or prosthesis, which implant or prosthesis comprises a biomaterial and the isolated heparin or heparan sulphate, into tissue of the patient at or surrounding the site of fracture.

In some embodiments the implant or prosthesis is coated with the isolated heparin or heparan sulphate. In some embodiments the implant or prosthesis is impregnated with the isolated heparin or heparan sulphate. In some embodiments the implant or prosthesis is further impregnated with BMP2 protein.

In yet a further aspect of the present invention a kit of parts is provided, the kit comprising a predetermined amount of the isolated heparin or heparan sulphate and a predetermined amount of BMP2. The kit may comprise a first container containing the predetermined amount of the isolated heparin or heparan sulphate and a second container containing the predetermined amount of BMP2. The kit may be provided for use in a method of medical treatment. The method of medical treatment may comprise a method of wound healing in vivo, the repair and/or regeneration of connective tissue, the repair and/or regeneration of bone and/or the repair and/or regeneration of bone in a mammal or a human. The kit may be provided together with instructions for the administration of the isolated heparin or heparan sulphate and BMP2 protein separately, sequentially or simultaneously in order to provide the medical treatment.

In a further aspect of the present invention products are provided, the products containing therapeutically effective amounts of:

(i) the isolated heparin or heparan sulphate; and
(ii) BMP2 protein;

for simultaneous, separate or sequential use in a method of medical treatment. The method of medical treatment may comprise a method of wound healing in vivo, the repair and/or regeneration of connective tissue, the repair and/or regeneration of bone and/or the repair and/or regeneration of bone in a mammal or a human. The products may optionally be formulated as a combined preparation for co-administration.

In a further aspect of the present invention there is provided a method of designing a heparin or heparan sulphate, optionally a heparin or heparan sulphate for use in a method of treatment as described herein, the method comprising determining one or more of the chain length, sulphation pattern and saccharide (or disaccharide) content or sequence of a heparin or heparan sulphate that has BMP2 binding activity.

In another aspect of the present invention there is provided a method of manufacturing, producing or preparing a heparin or heparan sulphate, optionally a heparin or heparan sulphate for use in a method of treatment as described herein, the method comprising one or more of the following steps:

(i) determining one or more of the chain length, sulphation pattern and saccharide (or disaccharide) content or sequence of a heparin or heparan sulphate that has BMP2 binding activity;

(ii) synthesising one or a plurality of heparin or heparan sulphate oligosaccharides having a chain length, and/or sulphation pattern and/or saccharide (or disaccharide) content or sequence correlated with BMP2 binding activity;

(iii) formulating one or a plurality of heparin or heparan sulphate oligosaccharides having a chain length, and/or sulphation pattern and/or saccharide (or disaccharide) content or sequence correlated with BMP2 binding activity as a pharmaceutical composition or medicament.

DETAILED DESCRIPTION OF THE INVENTION

In some embodiments heparin or heparan sulphate oligosaccharides may be obtained by size fractionation of heparin or heparan sulphate preparations. As such the heparin and heparan sulphate oligosaccharides may be fragments of larger heparin or heparan sulphate molecules. Suitable sources of heparin and heparan sulphate preparations for size fractionation include commercially available heparin and heparan sulphate preparations. For example, heparin sulphate preparations can be obtained during isolation of heparin from pig intestinal mucosa (e.g. available from Celsus Laboratories Inc., Sigma Aldrich, Iduron, UK).

Other suitable sources of heparin or heparan sulphate include heparin or heparan sulphate from any mammal (human or non-human), particularly from the kidney, lung or intestinal mucosa. In some embodiments the heparin or heparan sulphate is from pig (porcine) or cow (bovine) intestinal mucosa, kidney or lung.

In other embodiments the heparin and heparan sulphates oligosaccharides may be obtained by chemical synthesis of the desired oligosaccharide chain.

Heparin or heparan sulphate oligosaccharides or fragments according to the present invention may be provided in isolated form or in substantially purified form. This may comprise providing a composition in which the heparin or heparan sulphate oligosaccharide component is at least 80% heparin or heparan sulphate oligosaccharide, more preferably one of at least 85%, 90%, 95%, 96%, 97%, 98%, 99% or 100%.

Glycosaminglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulphate, keratan sulphate, heparin, dermatan sulphate, hyaluronate and heparan sulphate.

Heparin

Heparin is a highly sulphated glycosaminoglycan. The most common disaccharide unit in heparin is a 2-O-sulphated iduronic acid and 6-O-sulphated, N-sulphated glucosamine, IdoA(2S)-GlcNS(6S). This makes up about 85% of heparins from beef lung and about 75% of those from porcine intestinal mucosa. Although it is related to heparan sulphate, heparan sulphate differs from heparin in that heparan sulphate is normally composed of a glucuronic acid (GlcA) linked to N-acetylglucosamine (GlcNAc) which makes up around 50% of the total disaccharide units.

Heparan Sulphate (HS)

Heparan sulphate proteoglycans (HSPGs) represent a highly diverse subgroup of proteoglycans and are composed of heparan sulphate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulphate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulphation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulphotransferase (HSNDST), HS 2-O-sulphotransferase (HS2ST), HS 6-O-sulphotransferase (HS6ST) and HS 3-O-sulphotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulphate side chains consist of alternately arranged D-glucuronic acid or L-iduronic acid and D-glucosamine, linked via (1→4) glycosidic bonds. The glucosamine is often N-acetylated or N-sulphated and both the uronic acid and the glucosamine may be additionally O-sulphated. The specificity of a particular HSPG for a particular binding partner is created by the specific pattern of carboxyl, acetyl and sulphate groups attached to the glucosamine and the uronic acid. In contrast to heparin, heparan sulphate contains less N- and O-sulphate groups and more N-acetyl groups. The heparan sulphate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulphate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulphated sequences of sugar residues which are separated by unsulphated regions of disaccharides containing N-acetylated glucosamine. The initial conversion of N-acetylglucosamine to N-sulphoglucosamine creates a focus for other modifications, including epimerization of glucuronic acid to iduronic acid and a complex pattern of O-sulphations on glucosamine or iduronic acids. In addition, within the non-modified, low sulphated, N-acetylated sequences, the hexuronate residues remain as glucuronate, whereas in the highly sulphated N-sulphated regions, the C-5 epimer iduronate predominates. This limits the number of potential disaccharide variants possible in any given chain but not the abundance of each. Most modifications occur in the N-sulphated domains, or directly adjacent to them, so that in the mature chain there are regions of high sulphation separated by domains of low sulphation (Brickman et al. (1998), J. Biol. Chem. 273(8), 4350-4359, which is herein incorporated by reference in its entirety).

It is hypothesized that the highly variable heparan sulphate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulphate glycosaminoglycans may be genetically described (Alberts et al. (1989) Garland Publishing, Inc, New York & London, pp. 804 and 805), heparan sulphate glycosaminoglycan species isolated from a single source may differ in biological activity. As shown in Brickman et al, 1998, Glycobiology 8, 463, two separate pools of heparan sulphate glycosaminoglycans obtained from neuroepithelial cells could specifically activate either FGF-1 or FGF-2, depending on mitogenic status. Similarly, the capability of a heparan sulphate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulphation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC, capillary electrophoresis and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulphation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulphation patterns are found. Note: The repeating disaccharide backbone of the heparan polymer is a uronic acid connected to the amino sugar glucosamine. "NS" means the amino sugar is carrying a sulphate on the amino group enabling sulphation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography.

Chemical Synthesis of Heparin or Heparan Sulphate Oligosaccharides

Synthetic heparin or heparan sulphate oligosaccharides of defined length may be prepared using traditional solution phase chemistry with purification of products either by crystallization or flash column chromatography using Silicagel 60 (Fluka, Gillingham, UK). Oligosaccharides comprising 6 to 12 saccharide residues can be assembled from disaccharide precursors bearing protective groups. Final products can be purified by size exclusion chromatography using Sephadex G-25 (Sigma-Aldrich, Gillingham, UK) and lyophilised. Product structure and purity can be confirmed by NMR spectroscopy and mass spectrometry.

For example, the approach taken by Cole et al may be followed (Cole C L, Hansen S U, Baráth M, Rushton G, Gardiner J M, et al. (2010) Synthetic Heparan Sulphate Oligasaccharides Inhibit Endothelial Cell Functions Essential for Angiogenesis. PLoS ONE 5(7): e11644, doi:10.1371/journal.pone.0011644).

Synthetic heparin or heparan sulphates may be prepared as analogues of heparin or heparan sulphate oligosaccharides identified by size fractionation of preparations containing long chain length heparin or heparan sulphate oligosaccharides, such as commercially available heparin or heparan sulphate preparations from, e.g., porcine mucosa.

Synthetic heparin or heparan sulphate oligosaccharides may be prepared so as to have a specified chain length, sulphation pattern and disaccharide content, and the design of such oligosaccharides may be based on information about chain length, sulphation pattern and disaccharide content of heparin or heparan sulphate oligosaccharides identified by analysis of size fractionated preparations of heterogeneous heparin or heparan sulphate preparations, as described herein.

As such, in a further aspect of the present invention there is provided a method of designing a heparin or heparan sulphate, optionally a heparin or heparan sulphate, useful in a method of treatment as described herein, the method comprising determining one or more of the chain length, sulphation pattern and saccharide, (or disaccharide) content or sequence of a heparin or heparan sulphate that has BMP2 binding activity.

In another aspect of the present invention there is provided a method of manufacturing, producing or preparing a heparin or heparan sulphate, optionally a heparin or heparan sulphate useful in a method of treatment as described herein, the method comprising one or more of the following steps:

(i) determining one or more of the chain length, sulphation pattern and saccharide (or disaccharide) content or sequence of a heparin or heparan sulphate that has BMP2 binding activity;

(ii) synthesising one or a plurality of heparin or heparan sulphate oligosaccharides having a chain length, and/or sulphation pattern and/or saccharide (or disaccharide) content or sequence correlated with BMP2 binding activity;

(iii) formulating one or a plurality of heparin or heparan sulphate oligosaccharides having a chain length, and/or sulphation pattern and/or saccharide (or disaccharide) content or sequence correlated with BMP2 binding activity as a pharmaceutical composition or medicament.

HS3

HS3 is a BMP2 binding heparan sulphate, described in U.S. Pat. No. 9,498,494 and in WO2010/030244 (where it is called HS/BMP2), both incorporated herein in their entirety by reference.

HS3 is obtainable by methods of enriching mixtures of compounds containing one or more GAGs that bind to a polypeptide corresponding to the heparin-binding domain of BMP2. The enrichment process may be used to isolate HS3.

HS3 is believed to potentiate (e.g. agonize) the activity of BMP-2 and hence its ability to stimulate stem cell proliferation and bone formation.

In addition to being obtainable by the methodology described in U.S. Pat. No. 9,498,494 and in WO2010/030244, HS3 can also be defined functionally and structurally.

Functionally, HS3 is capable of binding a peptide having, or consisting of, the amino acid sequence of SEQ ID NO:1 (QAKHKQRKRLKSSCKRHP) or SEQ ID NO:2 (QAKHKQRKRLKSSCKRH), representing the heparin binding domain of BMP2. Preferably, HS3 binds the peptide of SEQ ID NO:1 or 2 with a $K_D$ of less than 100 µM, more preferably less than one of 50 µM, 40 µM, 30 µM, 20 µM, or 10 µM.

Preferably, HS3 also binds BMP2 protein with a $K_D$ of less than 100 µM, more preferably less than one of 50 µM, 40 µM, 30 µM, 20 µM, or 10 µM. Binding between HS3 and BMP2 protein may be determined by the following assay method.

BMP2 is dissolved in Blocking Solution (0.2% gelatin in SAB) at a concentration of 3 µg/ml and a dilution series from 0-3 µg/ml in Blocking Solution is established. Dispensing of 200 µl of each dilution of BMP2 into triplicate wells of Heparin/GAG Binding Plates pre-coated with heparin; incubated for 2 hrs at 37° C., washed carefully three times with SAB and 200 µl of 250 ng/ml biotinylated anti-BMP2 added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubate at room temperature for 40 minutes with absorbance reading at 405 nm within one hour.

In this assay, binding may be determined by measuring absorbance and may be determined relative to controls such as BMP2 protein in the absence of added heparan sulphate, or BMP2 protein to which an heparan sulphate is added that does not bind BMP2 protein.

The binding of HS3 is preferably specific, in contrast to non-specific binding and in the context that the HS3 can be selected from other heparan sulphates and/or GAGs by a method involving selection of heparan sulphates exhibiting a high affinity binding interaction with the peptide of SEQ ID NO:1 or 2 or with BMP2 protein.

HS3 according to the present invention preferably enhances BMP2 induced Alkaline Phosphatase (ALP) activity in cells of the mouse myoblast cell line C2C12 to a greater extent than the enhancement obtained by addition of corresponding amounts of BMP2 protein or Heparin alone. Preferably it also enhances BMP2-induced ALP activity in C2C12 cells to a greater extent than that induced by combined addition of corresponding amounts of BMP2 protein and heparin, or of BMP2 protein and a heparan sulphate that does not bind BMP2 protein with high affinity.

Enhancement of ALP activity can be measured by performing the following ALP Assay. C2C12 cells are plated at 20,000 cells/cm$^2$ in a 24-well plate in DMEM (e.g. Sigma-Aldrich Inc., St. Louis, Mo.) containing 10% FCS (e.g. Lonza Group Ltd., Switzerland) and antibiotics (1% Penicillin and 1% Streptomycin) (e.g. Sigma-Aldrich Inc., St. Louis, Mo.) at 37° C./5% CO$_2$. After 24 hours, the culture media is switched to 5% FCS low serum media containing different combinations of 100 ng/mL BMP2 (e.g. R&D Systems, Minneapolis, Minn.), 3 mg/mL Celsus HS and varying concentrations of BMP2-specific (+ve HS) and non-specific (−ve HS) Celsus HS preparations. Cell lysis is carried out after 3 days using RIPA buffer containing 1% Triton X-100, 150 mM NaCl, 10 mM Tris pH 7.4, 2 mM EDTA, 0.5% Igepal (NP40), 0.1% Sodium dodecyl sulphate (SDS) and 1% Protease Inhibitor Cocktail Set III (Calbiochem, Germany). The protein content of the cell lysate is determined by using BCA protein assay kit (Pierce Chemical Co., Rockford, Ill.). ALP activity in the cell lysates was then determined by incubating the cell lysates with p-nitrophenylphosphate substrate (Invitrogen, Carlsbad, Calif.). The reading is normalized to total protein amount and presented as relative amount to the group containing BMP2 treatment alone.

Enhancement of ALP activity in C2C12 cells can also be followed by immunohistochemical techniques, such as the following an ALP staining protocol. ALP Staining. C2C12 cells are cultured as described in the assay methodology immediately above. After 3 days of treatment, the cell layer is washed in PBS and stained using Leukocyte Alkaline Phosphatase Kit (e.g. Sigma-Aldrich Inc., St. Louis, Mo.) according to manufacturer's specification. The cell layer is fixed in citrate buffered 60% acetone and stained in alkaline-dye mixture containing Naphthol AS-MX Phosphatase Alkaline and diazonium salt. Nuclear staining is performed using Mayer's Hematoxylin solution.

These techniques can be used to identify HS3 as a heparan sulphate that enhances a greater degree of BMP2 protein induced ALP activity in C2C12 cells compared with non-specific heparan sulphates, e.g. heparan sulphates that do not bind BMP-2 protein.

HS3 prolongs the effects of BMP2 signalling to levels that equal or exceed those of heparin. This can be assessed by the following assay. C2C12 cells are exposed to (i) nothing, (ii) BMP2 alone, (iii) BMP2+Heparin or (iv) BMP2+HS3 for 72 hours and the phosphorylation levels of the BMP2-specific intracellular signaling molecule Smad1/5/8 are monitored by immunoblotting.

An important functional property of HS3 is its ability to enhance the process of bone repair, particularly in mammalian subjects. This may be tested in a bone repair model, in which the speed and quality of bone repair in control animals (e.g. animals not given HS or animals given an HS that does not bind BMP2 protein or the peptide of SEQ ID NO:1 or 2) and HS3 treated animals is compared. Speed and quality of bone repair may be assessed by analysing generation of bone volume at the wound site over time, e.g. by X-ray and microCT imaging analysis of the wound.

Recent research has shown that gamma-irradiation does not affect HS3 binding affinity toward BMP2. Furthermore, irradiation did not significantly affect HS3's ability to synergistically enhance the osteogenic effects of BMP2. This confirmed that gamma-irradiation can be utilised for the sterilisation of HS3 products without affecting biological activity. Therefore HS3 could be incorporated into orthotic implants, scaffolds and other medical devices, that need to be sterilised by such methods, for use in the treatment of a range of diseases and disorders [33].

Structurally, N-sulfation of N-acetyl-D-glucosamine (GlcNAc) residues in HS3 has been found to be important as regards maintaining binding affinity for BMP2 protein. N-desulfation was shown to lead to a significant reduction in BMP2 protein binding affinity.

6-O-sulfation (O-sulphation at C6) of N-sulphoglucosamine (GlcNS) residues was also found to be of moderate significance as regards maintaining binding affinity for BMP2 protein. 6-O-desulfation led to some reduction in BMP2 protein binding affinity.

2-O-sulfation (O-sulphation at C2) of IdoA and/or D-glucuronic acid (GlcA) residues was found not to affect BMP2 protein binding. As such, HS3 may optionally be either 2-O-sulfated or 2-O-desulfated.

The disaccharide composition of HS3 may be determined by digestion with heparin lyases I, II and III to completion and then subjecting the resulting disaccharide fragments to capillary electrophoresis analysis.

HS3 includes heparan sulphate that has a disaccharide composition within ±10% (more preferably ±one of 9%, 8%, 7%, 6%, 5%, 4%, 3%, 2%, 1% or 0.5%) of the values shown for each disaccharide in the table below, as determined respectively by lyase digestion and SAX-HPLC analysis or digestion with heparin lyases I, II and III to completion and then subjecting the resulting disaccharide fragments to capillary electrophoresis analysis.

| Disaccharide | Normalised weight percentage |
| --- | --- |
| ΔHexUA, 2SGlcNS, 6S | 14.8 |
| ΔHexUA, 2S-GlcNS | 4.9 |
| ΔHexUA-GlcNS, 6S | 11.1 |
| ΔHexUA, 2SGlcNAc, 6S | 4.8 |
| ΔHexUA-GlcNS | 22.2 |
| ΔHexUA, 2S-GlcNAc | 1.1 |
| ΔHexUA-GlcNAc, 6S | 10.1 |
| ΔHexUA-GlcNAc | 31.1 |

The disaccharide composition of HS3 as determined by digestion with heparin lyases I, II and III to completion and then subjecting the resulting disaccharide fragments to capillary electrophoresis analysis may have a disaccharide composition according to any one of the following:

| Disaccharide | Normalised weight percentage |
| --- | --- |
| ΔHexUA, 2SGlcNS, 6S | 14.8 ± 3.0 |
| ΔHexUA, 2S-GlcNS | 4.9 ± 2.0 |
| ΔHexUA-GlcNS, 6S | 11.1 ± 3.0 |
| ΔHexUA, 2SGlcNAc, 6S | 4.8 ± 2.0 |
| ΔHexUA-GlcNS | 22.2 ± 3.0 |
| ΔHexUA, 2S-GlcNAc | 1.1 ± 0.5 |
| ΔHexUA-GlcNAc, 6S | 10.1 ± 3.0 |
| ΔHexUA-GlcNAc | 31.1 ± 3.0 | or

| Disaccharide | Normalised weight percentage |
| --- | --- |
| ΔHexUA, 2SGlcNS, 6S | 14.8 ± 2.0 |
| ΔHexUA, 2S-GlcNS | 4.9 ± 2.0 |
| ΔHexUA-GlcNS, 6S | 11.1 ± 2.0 |
| ΔHexUA, 2SGlcNAc, 6S | 4.8 ± 2.0 |
| ΔHexUA-GlcNS | 22.2 ± 2.0 |
| ΔHexUA, 2S-GlcNAc | 1.1 ± 0.5 |
| ΔHexUA-GlcNAc, 6S | 10.1 ± 2.0 |
| ΔHexUA-GlcNAc | 31.1 ± 2.0 | or

| Disaccharide | Normalised weight percentage |
| --- | --- |
| ΔHexUA, 2SGlcNS, 6S | 14.8 ± 2.0 |
| ΔHexUA, 2S-GlcNS | 4.9 ± 1.0 |
| ΔHexUA-GlcNS, 6S | 11.1 ± 2.0 |
| ΔHexUA, 2SGlcNAc, 6S | 4.8 ± 1.0 |
| ΔHexUA-GlcNS | 22.2 ± 2.0 |
| ΔHexUA, 2S-GlcNAc | 1.1 ± 0.5 |
| ΔHexUA-GlcNAc, 6S | 10.1 ± 2.0 |
| ΔHexUA-GlcNAc | 31.1 ± 3.0 | or

| Disaccharide | Normalised weight percentage |
| --- | --- |
| ΔHexUA, 2SGlcNS, 6S | 14.8 ± 1.0 |
| ΔHexUA, 2S-GlcNS | 4.9 ± 0.4 |
| ΔHexUA-GlcNS, 6S | 11.1 ± 1.0 |
| ΔHexUA, 2SGlcNAc, 6S | 4.8 ± 0.6 |
| ΔHexUA-GlcNS | 22.2 ± 3.0 |
| ΔHexUA, 2S-GlcNAc | 1.1 ± 0.4 |
| ΔHexUA-GlcNAc, 6S | 10.1 ± 1.0 |
| ΔHexUA-GlcNAc | 31.1 ± 1.6 | or

| Disaccharide | Normalised weight percentage |
| --- | --- |
| ΔHexUA, 2SGlcNS, 6S | 14.8 ± 0.75 |
| ΔHexUA, 2S-GlcNS | 4.9 ± 0.3 |
| ΔHexUA-GlcNS, 6S | 11.1 ± 0.75 |
| ΔHexUA, 2SGlcNAc, 6S | 4.8 ± 0.45 |
| ΔHexUA-GlcNS | 22.2 ± 2.25 |
| ΔHexUA, 2S-GlcNAc | 1.1 ± 0.3 |
| ΔHexUA-GlcNAc, 6S | 10.1 ± 0.75 |
| ΔHexUA-GlcNAc | 31.1 ± 1.2 | or

| Disaccharide | Normalised weight percentage |
| --- | --- |
| ΔHexUA, 2SGlcNS, 6S | 14.8 ± 0.5 |
| ΔHexUA, 2S-GlcNS | 4.9 ± 0.2 |
| ΔHexUA-GlcNS, 6S | 11.1 ± 0.5 |
| ΔHexUA, 2SGlcNAc, 6S | 4.8 ± 0.3 |
| ΔHexUA-GlcNS | 22.2 ± 1.5 |
| ΔHexUA, 2S-GlcNAc | 1.1 ± 0.2 |
| ΔHexUA-GlcNAc, 6S | 10.1 ± 0.5 |
| ΔHexUA-GlcNAc | 31.1 ± 0.8 |

Digestion of HS3 with heparin lyases I, II and III and/or capillary electrophoresis analysis of disaccharides may be preferably performed as described in Example 10 of U.S. Pat. No. 9,498,494.

Digestion of HS preparations with heparin lyase enzymes may be conducted as follows: HS preparations (1 mg) are each dissolved in 500 μL of sodium acetate buffer (100 mM containing 10 mM calcium acetate, pH 7.0) and 2.5 mU each of the three enzymes is added; the samples are incubated at 37° C. overnight (24 h) with gentle inversion (9 rpm) of the sample tubes; a further 2.5 mU each of the three enzymes is added to the samples which are incubated at 37° C. for a further 48 h with gentle inversion (9 rpm) of the sample tubes; digests are halted by heating (100° C., 5 min) and are then lyophilized; digests are resuspended in 500 μL water and an aliquot (50 μL) is taken for analysis.

Capillary electrophoresis (CE) of disaccharides from digestion of HS preparations may be conducted as follows: capillary electrophoresis operating buffer is made by adding an aqueous solution of 20 mM $H_3PO_4$ to a solution of 20 mM $Na_2HPO_4.12H_2O$ to give pH 3.5; column wash is 100 mM NaOH (diluted from 50% w/w NaOH); operating buffer and column wash are both filtered using a filter unit fitted with 0.2 μm cellulose acetate membrane filters; stock solutions of disaccharide Is (e.g. 12) are prepared by dissolving the disaccharides in water (1 mg/mL); calibration curves for the standards are determined by preparing a mix containing all standards containing 10 μg/100 μL of each disaccharide and a dilution series containing 10, 5, 2.5, 1.25, 0.625, 0.3125 μg/100 μL is prepared; including 2.5 μg of internal standard (ΔUA,2S-GlcNCOEt,6S). The digests of HS are diluted (50 μL/mL) with water and the same internal standard is added (2.5 μg) to each sample. The solutions are freeze-dried and re-suspended in water (1 mL). The samples are filtered using PTFE hydrophilic disposable syringe filter units.

Analyses are performed using a capillary electrophoresis instrument on an uncoated fused silica capillary tube at 25° C. using 20 mM operating buffer with a capillary voltage of 30 kV. The samples are introduced to the capillary tube using hydrodynamic injection at the cathodic (reverse polarity) end. Before each run, the capillary is flushed with 100 mM NaOH (2 min), with water (2 min) and pre-conditioned with operating buffer (5 min). A buffer replenishment system replaces the buffer in the inlet and outlet tubes to ensure consistent volumes, pH and ionic strength are maintained. Water only blanks are run at both the beginning, middle and end of the sample sequence. Absorbance is monitored at 232 nm. All data is stored in a database and is subsequently retrieved and re-processed.

Duplicate or triplicate digests/analyses may be performed and the normalized percentage of the disaccharides in the HS digest is calculated as the mean average of the results for the analyses.

HS3 exhibits high affinity binding to BMP2 protein or the peptide of SEQ ID NO:1 or 2.

The structural differences of HS3 compared with heparan sulphates that do not bind BMP2 protein may also be illustrated by conducting surface plasmon resonance analysis. For example, the angle shift can be used to distinguish HS3 from other heparan sulphates.

Fragments of HS3

Some aspects and embodiments of the present invention concern fragments of HS3, or mixtures comprising fragments of HS3.

Preferably a fragment of HS3, is an oligosaccharide chain of HS3 that has been truncated, cleaved or divided, e.g. by action of a lyase of an HS3 oligosaccharide chain to create more than one shorter chain. Preferred fragments are those that retain the ability to bind BMP2, enhance BMP2-mediated ALP activity, enhance BMP2 mediated Smad 1/5/9 phosphorylation and/or enhance bone repair.

HS3 fragments and mixtures of HS3 fragments preferably exclude full length BMP2 binding heparan sulfate, such as HS3.

Full length HS3 typically has an average chain length of about 50 saccharides or more, and an average molecular weight of about 15 kDa. As such, HS3 fragments and mixtures of HS3 fragments may have less than 10% oligosaccharide chains that have a chain length of greater than 50 saccharides. Optionally, this may be a percentage selected from one of 5%, 10%, 15%, 20%, 25%, 30%, 35%, 40%, 45%, 50%, 55%, 60%, 65%, 70%, 75%, 80%, 85%, 90%, or 95%.

Mixtures of Heparin or Heparin Sulphate Oligosaccharides

Mixtures may comprise a plurality of oligosaccharide chains each of the plurality having defined length in terms of number or saccharides and, optionally, in terms of functional properties such as BMP2 binding.

The mixture may be heterogeneous in terms of the oligosaccharide content, for example it may contain oligosaccharides according to the invention of varying length but all within a defined length range.

A mixture may contain other components, e.g. other glycosaminoglycans or heparin or heparan sulphate species. In some embodiments the mixture does not contain glycosaminoglycans, heparin or heparan sulphate species that are different to the oligosaccharides according to the present invention.

Formulating Pharmaceutically Useful Compositions and Medicaments

In accordance with the present invention methods are also provided for the production of pharmaceutically useful compositions, which may be based on an identified heparin or heparan sulphate. Such methods of production may further comprise one or more steps selected from:

(a) identifying and/or characterising the structure of a selected heparin or heparan sulphate;

(b) obtaining the heparin or heparan sulphate;
(c) mixing the selected heparin or heparan sulphate with a pharmaceutically acceptable carrier, adjuvant or diluent.

For example, a further aspect of the present invention relates to a method of formulating or producing a pharmaceutical composition for use in a method of treatment, the method comprising:

(i) identifying and/or isolating the heparin or heparan sulphate; and/or
(ii) formulating a pharmaceutical composition by mixing the heparin or heparan sulphate, with a pharmaceutically acceptable carrier, adjuvant or diluent.

Certain pharmaceutical compositions formulated by such methods may comprise a prodrug of the selected substance wherein the prodrug is convertible in the human or animal body to the desired active agent. In other cases the active agent may be present in the pharmaceutical composition so produced and may be present in the form of a physiologically acceptable salt.

Biomaterials

Pharmaceutical compositions and medicaments of the invention may take the form of a biomaterial that is coated and/or impregnated with isolated heparin or heparan sulphate. An implant or prosthesis may be formed from the biomaterial. Such implants or prostheses may be surgically implanted to assist in transplantion of cells.

The isolated heparin or heparan sulphate may be applied to implants or prostheses to accelerate new tissue formation at a desired location. It will be appreciated that heparins and heparan sulphates, unlike proteins, are particularly robust and have a much better ability to withstand the solvents required for the manufacture of synthetic bioscaffolds and application to implants and prostheses.

The biomaterial may be coated or impregnated with the isolated heparin or heparan sulphate. Impregnation may comprise forming the biomaterial by mixing the isolated heparin or heparan sulphate with the constitutive components of the biomaterial, e.g. during polymerisation, or absorbing the isolated heparin or heparan sulphate into the biomaterial. Coating may comprise adsorbing the isolated heparin or heparan sulphate onto the surface of the biomaterial.

The biomaterial should allow the coated or impregnated the isolated heparin or heparan sulphate to be released from the biomaterial when administered to or implanted in the subject. Biomaterial release kinetics may be altered by altering the structure, e.g. porosity, of the biomaterial.

In addition to coating or impregnating a biomaterial with the isolated heparin or heparan sulphate, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. In addition or alternatively to the above bioactive molecules, one or more bisphosphonates may be impregnated or coated onto the biomaterial along with the isolated heparin or heparan sulphate. Examples of useful bisphosphonates may include at least one chosen from the group consisting of: etidronate; clodronate; alendronate; pamidronate; risedronate; zoledronate.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades. Alternatively a non-biodegradable biomaterial may be used with surgical removal of the biomaterial being an optional requirement.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulphone, polyurethane, polyacrylonitrile, sulphonated polysulphone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices.* 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications.* 2000; 14(3); 229-242; DeBlois Cote M F. Doillon C J. Heparin-fibroblast growth factor fibrin complex: in vitro and in vivo applications to collagen based materials. *Biomaterials.* 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

Other suitable biomaterials include ceramic or metal (e.g. titanium), hydroxyapatite, tricalcium phosphate, demineralised bone matrix (DBM), autografts (i.e. grafts derived from the patients tissue), or allografts (grafts derived from the tissue of an animal that is not the patient). Biomaterials may be synthetic (e.g. metal, fibrin, ceramic) or biological (e.g. carrier materials made from animal tissue, e.g. non-human mammals (e.g. cow, pig), or human).

The biomaterial can be supplemented with additional cells. For example, one can "seed" the biomaterial (or co-synthesise it) with stem cells.

In one embodiment the biomaterial may comprise be coated or impregnated with the isolated heparin or heparan sulphate, and further comprise BMP2 (e.g. as a further coating or impregnated component) and cells, e.g. stem cells, adhered to the biomaterial.

Bone Fracture

In some aspects the present invention is concerned with the therapeutic use (human and veterinary) of the isolated heparin or heparan sulphate to treat bone fracture. The isolated heparin or heparan sulphate is reported here to augment wound healing in bone. The isolated heparin or heparan sulphate stimulates bone regeneration following injury and contributes to improved wound healing in bone. The isolated heparin or heparan sulphate provides improvements in the speed of bone fracture repair enabling a reduction in the recovery time from injury.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using heparin or heparan sulphate oligosaccharide include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using heparin or heparan sulphate oligosaccharide include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using heparin or heparan sulphate oligosaccharide also include those of the head (skull) and neck, including those of the face such as the jaw, nose and cheek. In this respect, in some preferred embodiments heparin or heparan sulphate oligosaccharide may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Although not limiting to the present invention, the primary actions of the isolated heparin or heparan sulphate may be on cells within, adjacent to, or caused to migrate into the wound site and may be on the bone stem cells, the preosteoblasts or the osteoblasts, or on any of the ancillary or vasculogenic cells found or caused to migrate into or within the wound bed.

The isolated heparin or heparan sulphate and pharmaceutical compositions and medicaments comprising the isolated heparin or heparan sulphate are provided for use in a method of treatment of bone fracture in a mammalian subject.

Treatment may comprise wound healing in bone. The treatment may involve repair, regeneration and growth of bone. The isolated heparin or heparan sulphate oligosaccharide facilitates fracture repair by facilitating new bone growth. The isolated heparin or heparan sulphate oligosaccharide acts to improve the speed of fracture repair enabling bone healing to occur faster leading to improved recovery time from injury. Treatment may lead to improved bone strength.

Administration of heparin or heparan sulphate oligosaccharide is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably isolated heparin or heparan sulphate is formulated in fluid or liquid form for injection.

In some embodiments the isolated heparin or heparan sulphate is formulated as a controlled release formulation, e.g. in a drug capsule for implantation at the wound site. The isolated heparin or heparan sulphate may be attached to, impregnated on or soaked into a carrier material (e.g. a biomaterial) such as nanofibres or biodegradable paper or textile.

Pharmaceutical compositions, medicaments, implants and prostheses comprising the isolated heparin or heparan sulphate oligosaccharide may also comprise BMP2. Owing to the ability of the isolated heparin or heparan sulphate oligosaccharide to bind BMP2, the isolated heparin or heparan sulphate oligosaccharide may act as a carrier of BMP2 assisting in delivery of BMP2 to the wound site and maintenance of BMP2 stability.

Administration is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of isolated heparin or heparan sulphate doses may be administered in accordance with the guidance of the prescribing medical practitioner. Purely by way of example, isolated heparin or heparan sulphate may be delivered in dosages of at least 1 ng/ml, more preferably at least 5 ng/ml and optionally 10 ng/ml or more. Individual dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

Isolated heparin or heparan sulphate may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required isolated heparin or heparan sulphate may be administered directly to (e.g. applied to) the fracture during the surgical procedure.

BMP2 Protein

In this specification BMP2 refers to Bone morphogenetic protein 2 (also called bone morphogenic protein 2, BMP2 or BMP-2), which is a member of the TGF-β superfamily and is implicated in the development of bone and cartilage.

The amino acid sequence of bone morphogenetic protein 2 preprotein from Homo sapiens can be found in GenBank under NCBI Accession No. NP_001191 (NP_001191.1 GI:4557369) in which amino acids 1 to 23 represent the signal peptide, and amino acids 24 to 396 represent the amino acid sequence of the proprotein.

In this specification "BMP2 protein" includes proteins having at least 70%, more preferably one of 75%, 80%, 85%, 90%, 95%, 96%, 97%, 98%, 99% or 100% sequence identity with the amino acid sequence of the BMP2 preprotein or BMP2 proprotein or with the amino acid sequence of the mature BMP2 protein.

The BMP2 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

In this specification a subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle (including cows, e.g. dairy cows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Methods according to the present invention may be performed in vitro or in vivo, as indicated. The term "in vitro" is intended to encompass procedures with cells in culture whereas the term "in vivo" is intended to encompass procedures with intact multi-cellular organisms.

The invention includes the combination of the aspects and preferred features described except where such a combination is clearly impermissible or expressly avoided.

The features disclosed in the foregoing description, or in the following claims, or in the accompanying drawings, expressed in their specific forms or in terms of a means for performing the disclosed function, or a method or process for obtaining the disclosed results, as appropriate, may, separately, or in any combination of such features, be utilised for realising the invention in diverse forms thereof.

While the invention has been described in conjunction with the exemplary embodiments described above, many equivalent modifications and variations will be apparent to those skilled in the art when given this disclosure. Accordingly, the exemplary embodiments of the invention set forth above are considered to be illustrative and not limiting. Various changes to the described embodiments may be made without departing from the spirit and scope of the invention.

For the avoidance of any doubt, any theoretical explanations provided herein are provided for the purposes of improving the understanding of a reader. The inventors do not wish to be bound by any of these theoretical explanations.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

Throughout this specification, including the claims which follow, unless the context requires otherwise, the word "comprise" and "include", and variations such as "comprises", "comprising", and "including" will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Ranges may be expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

All references mentioned above are hereby incorporated by reference.

EXAMPLES

In the following examples, the inventors describe the generation of heparan sulfate and heparin oligosaccharides with variable sizes. Additionally, the inventors demonstrate that heparan sulfate and heparin oligosaccharides fragments with reduced chain lengths can function as effectively as full length molecules.

Example 1: Methods to Determine Minimum Structural Requirements for BMP-2-Binding of Heparin Oligosaccharides 1.1. Materials All cell culture reagents, chemicals and heparin were purchased from Sigma-Aldrich (U.S.A.). Recombinant BMP-2 was purchased from R&D Systems Inc. (U.S.A.). Smad 1/5/8 antibody was purchased from Santa Cruz Biotechnology (Cat. #sc-6301-R; U.S.A.). Phospho-smad1/5/9 antibody (equivalent to phospho-smad1/5/8) was purchased from Cell Signaling Technologies (Cat. #13820; U.S.A.). Actin antibody (Cat. #MAB1501R) and protease inhibitor cocktail III were purchased from Merck-Millipore (U.S.A.). QIAzol lysis reagent was purchased from Qiagen (Germany). SYPRO orange, Superscript® Vilo™ cDNA synthesis kit, TaqMan® gene expression assays and TaqMan® Fast universal PCR mastermix, Pierce BCA protein assay kit, SuperSignal West Pico Chemiluminescent substrate, N-hydroxysuccinimide (NHS)-biotin and Zeba® spin 7 kDa MWCO desalting columns were purchased from Thermo-Fischer (U.S.A.). Size-defined heparin oligosaccharides (dp4-dp20) and selectively desulfated heparins were purchased from Iduron (U.K.). The C2C12 murine myoblast cell line was purchased from the American Type Culture Collection (ATCC). Hyperfilm, Superdex 200 HR (10×300 mm) and Sensor Chip SA were purchased from GE Healthcare (Sweden). Polycaprolactone (PCL) tubes (dimensions of 4.5 mm inner diameter, 3 mm height and 1 mm wall thickness) were purchased from Osteopore International Pte Ltd (Singapore). Collagen sponges were obtained from Integra LifeSciences Corp (U.S.A.) and measured 7×21×5 mm. Each sponge was cut evenly into 6 pieces with a sterile blade prior to implantation.

1.2. Surface Plasmon Resonance BMP-2 Competitive Binding Assay

Figure 1:
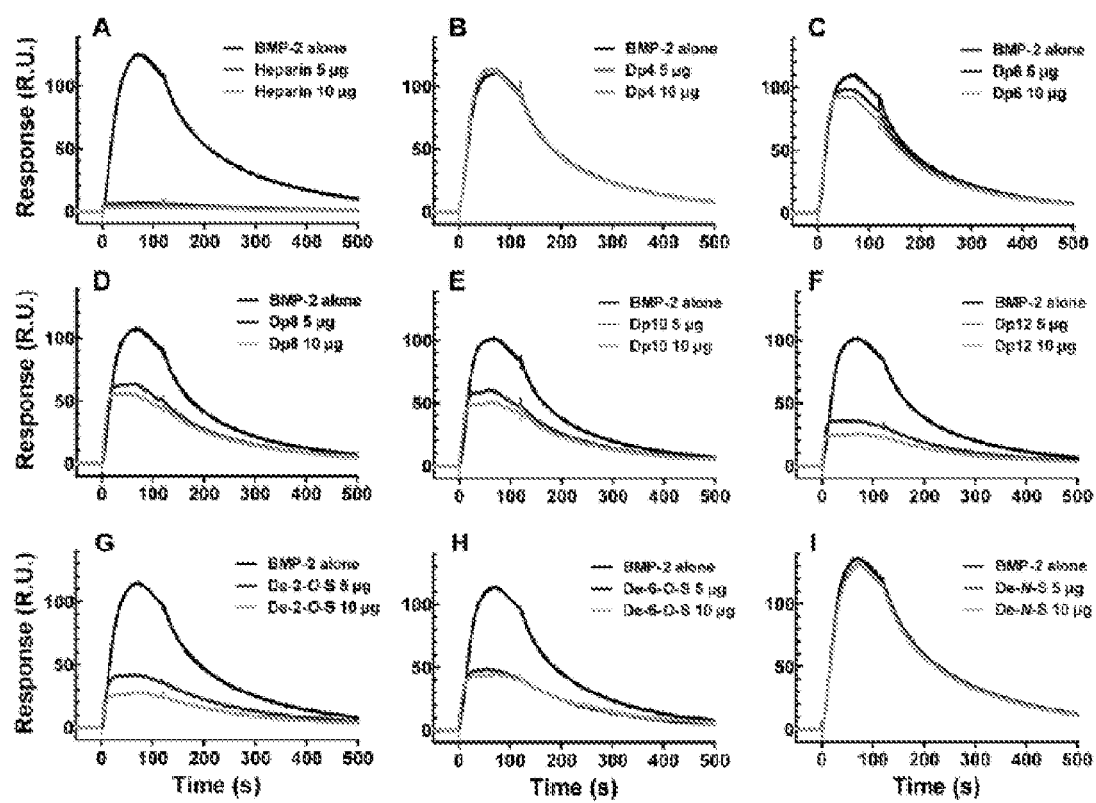
FIG. 1A to 1I. SPR competition binding assay sensorgrams. Representative sensorgrams generated from competitive binding experiments performed via SPR. BMP-2 (25 nM) was pre-incubated with a variety of heparin oligosaccharides (5 µg or 10 µg) and applied to a heparin-derivitised surface. SPR sensorgrams for heparin (A), dp4 (B), dp6 (C), dp8 (D), dp10 (E), dp12 (F), de-2-O-sulfated heparin (G), de-6-O-sulfated heparin (H) and de-N-sulfated heparin (I) display variable reduction in response over BMP-2 alone. All sensorgrams are representative of three independent experiments.

Interactions between BMP-2 and heparin oligosaccharides were measured via competitive inhibition of BMP-2 binding to a heparin-coated sensor chip using surface plasmon resonance, as described by Lee et al [27]. Briefly, 20 mg heparin was biotinylated at free amine groups using 8.6 μM NHS-biotin in dimethyl sulfoxide, after which excess unreacted NHS-biotin was removed by passing the sample through two 7 kDa molecular weight cut-off Zeba spin desalting columns. Using the inbuilt immobilization program on a Biacore T100 SPR system (GE healthcare), a sensor chip SA (GE healthcare) was coated with heparin-biotin in HBS-EP 0.05% buffer (150 mM NaCl, 10 mM HEPES, 3 mM EDTA, 0.05% (v/v) Tween-20, pH 7.4) at a flow rate of 30 μL/min until ~40 response units (R.U.) were achieved (where 1 R.U. is equal to ~1 pg of heparin/mm2). Dosing experiments were performed with BMP-2 with a range of concentrations from 6.25 nM to 100 nM, after which a dose of 25 nM was selected for competitive inhibition experiments. Heparin oligosaccharides were used at a concentration of 10 μg/mL in HBS-EP 0.1% buffer (HBS-EP with 0.1% (v/v) Tween-20). BMP-2 alone or BMP-2+heparin were applied to the chip for 120 s at 30 μL/min, followed by a 600 s dissociation period of HBS-EP 0.1% alone, after which the heparin surface was regenerated by two injections of 2 M NaCl in HBS-EP 0.1% for 60 s at 30 μL/min. The response was measured as a function of time at 25° C. R.U.s for the heparin surface were determined by subtracting the R.U. of the control (uncoated) flow channel from those of the heparin-biotin-coated flow channel. Representative sensorgrams from all competitive binding experiments may be found in supplementary information (FIG. 1). Results were normalized to the response of BMP-2 alone (100% response) and represented as the percentage reduction in response units vs. BMP-2 alone. Data constitutes the mean±S.D. of three independent experiments.

1.3. Differential Scanning Fluorimetry/BMP-2 Thermal Stability Assay

The ability of heparin oligosaccharides to improve the thermal stability of BMP-2 was assessed via differential scanning fluorimetry (DSF). Briefly, BMP-2 (5 μM), heparin oligosaccharides (50 μM), urea (5 M), HCl (400 μM), SYPRO orange (×50) and PBS were gently mixed and aliquoted into triplicate wells of a 96-well optical PCR plate (Axygen). Experiments were performed using a Quantstudio 6 real time PCR machine (Applied Biosciences) using the following heating cycle; 120 s incubation at 31° C. followed by 0.5° C. increases every 20 s to 81° C. Data was acquired using detection settings for TAMRA dye (γex 560 nm; γem 582 nm). BMP-2 melting temperature was determined by an observable peak in fluorescence emission generated by the binding of SYPRO dye to the core of the denatured protein. The highest temperatures determined from the first derivative of the melt curve from each replicate were selected and the relative stabilizing effect of each oligosaccharide vs. heparin was assessed using the following equation;

$$\frac{Tm\ X - Tm\ BMP2}{Tm\ \text{heparin} - Tm\ BMP2}$$

Where Tm=melting temperature, X=oligosaccharide+BMP-2, BMP2=BMP-2 alone and heparin=heparin+BMP-2). Data is represented as the mean±S.D. of three independent experiments.

1.4. Size-Exclusion Chromatography

A Superdex 200 HR column (300×10 mm, GE Healthcare) was equilibrated using a Dionex ICS 3000 series High Performance Liquid Chromatography (HPLC) system at a flow rate of 0.5 ml/min with running buffer (10 mM HEPES, pH 7.2, and 150 mM NaCl). Heparin fragments (25 μM) were incubated in the presence or absence of BMP-2 (25 μM) for 15 min at room temperature in running buffer, after which samples were loaded onto the column and eluted under isocratic flow at 0.5 ml/min. Elution of samples was monitored via absorbance at 232 nm (heparin) and 280 nm (BMP-2). All chromatographs are representative of three independent experiments.

1.5. Detection of Phosphorylated Forms of Smad 1/5/9 by Western Blotting

C2C12 murine myoblast cells were cultured in DMEM, 10% FCS and 100 U/mL penicillin/streptomycin at 37° C. in 5% CO2. For experiments, cells were seeded at 2×104 cells/cm2 in tissue culture treated 12-well plates. After 24 h, cells were washed and media was replaced with treatment media (maintenance media with 5% FCS) with or without BMP-2 (100 ng/mL) and heparin, heparin oligosaccharides or desulfated heparins (5 μg/mL). At the indicated time points (24, 48 and 72 h), cells were washed with PBS and lysed with RIPA buffer in the presence of protease inhibitors (Merck-Millipore). Total protein was quantified using the BCA assay and subsequently separated by SDS-PAGE (5 μg total protein per condition). Proteins were then transferred to nitrocellulose membranes and blocked for 1 h in blocking buffer (Tris-buffered saline containing 5% (w/v) non-fat dry milk and 0.05% (v/v) Tween 20). Incubation with primary antibodies diluted at 1:1000 (pSmad 1/5/9), 1:500 (Smad 1/5/8) or 1:5000 (actin) was carried out overnight at 4° C. in blocking solution. Membranes were washed three times with Tris-buffered saline containing 0.05% (v/v) Tween 20 and incubated with IgG-specific peroxidase-conjugated secondary antibodies, diluted 1:10000 in blocking buffer. Blots were then washed and developed using SuperSignal West Pico Chemiluminescent substrate (Thermo Scientific) on Hyperfilm (GE Healthcare) and scanned. Blots are representative of three independent experiments.

1.6. Analysis of Osteogenic Transcript Expression Via Quantitative Real Time PCR C2C12 cells were maintained and seeded as described above. Cells were treated with or without BMP-2 (100 ng/mL) with heparin, heparin oligosaccharides, or selectively desulfated heparins (5 μg/mL). The cells were cultured in treatment media for 3 days, after which total RNA was harvested using QIAzol lysis reagent (Qiagen) according to manufacturer's instructions. Total RNA was quantified via Nanodrop 2000 and 1 μg total RNA was reverse transcribed to generate complementary DNA (cDNA) using SuperScript Vilo (Thermo-Fisher) according to manufacturer's instructions. Quantitative real-time PCR (qPCR) was performed using a Quantstudio 6 real-time PCR machine, using 40 ng of cDNA per reaction in conjunction with TaqMan® gene expression assays (Thermo-Fisher). Transcription of osteogenesis-associated genes of interest were analyzed using the following TaqMan® gene expression assays; alpl (Mm00475834_m1), sp7 (Mm04209856_m1) and runx2 (Mm00501584_m1). Ribosomal RNA 18s (Mm04277571_s1) was used as an internal control. Data was analyzed using the ΔΔCt method and normalized to treatment with BMP-2 alone. Data is expressed as mean fold change ±S.D. of three independent experiments.

1.7. Alkaline Phosphatase Activity Assay

C2C12 cells were maintained as described above and seeded at 2×104 cells/cm2 in tissue culture treated 24-well plates. The cells were cultured in treatment media for 3 days, after which total protein was extracted and ALP activity was determined. Briefly, cells were washed with PBS and total protein extracted with RIPA buffer containing a protease inhibitor cocktail. Total protein concentration was determined using the BCA assay, then 7.5 μg of total protein per condition was combined with p-nitrophenylphosphate (Thermo-Fisher). Absorbance was measured at 405 nm via spectrophotometry and expressed as relative ALP activity normalized to the BMP-2 alone treatment group. Data represents mean±S.D. of three independent experiments.

1.8. Osteogenic Differentiation and Mineralization

C2C12 cells were maintained as described above and seeded at 5×103 cells/cm2 in tissue culture treated 12-well plates. Cells were cultured in osteogenic media (DMEM low glucose, 5% (v/v) FCS, 100 U/mL penicillin/streptomycin, 10 mM μ-glycerophosphate and 50 μg/mL ascorbic acid 2-phosphate) with or without BMP-2 (100 ng/mL) and heparin variants (5 μg/mL) for 12 days, with media being replenished every three days. Cells were washed with PBS and fixed with ice cold methanol for 20 min at −20° C. After fixation, cells were washed with water and stained with Alizarin red solution (0.1% (w/v), pH 4.3) for 20 min at room temperature with gentle agitation. Cells were then washed three times with water and imaged using a scanner. Alizarin red dye was extracted with 10% (v/v) acetic acid, neutralized with 10% (w/v) ammonium hydroxide and quantified using spectrophotometry (absorbance at 405 nm). Images are representative of at least three independent experiments and quantified Alizarin red stain represents mean±S.D. of three independent experiments.

1.9. Ectopic Bone Formation Assay

Thirteen female, Sprague Dawley rats weighing 120-150 g had four hind limb muscle pockets surgically created, two per limb [48]. Each pocket was randomly filled with one of the following treatments; (1) Polycaprolactone tube (PT), (2) PT+collagen sponge (CS) (Ctrl), (3) PT+CS+BMP-2 (5 μg), (4) PT+CS+heparin (25 μg)+BMP-2 (5 μg), (5) PT+CS+dp8 (25 μg)+BMP-2 (5 μg), (6) PT+CS+dp10 (25 μg)+BMP-2 (5 μg), (7) PT+CS+dp12 (25 μg)+BMP-2 (5 μg), (8) PT+CS+de-2-O sulfated heparin (25 μg)+BMP-2 (5 μg) (9) PT+CS+de-6-O sulfated heparin (25 μg) +BMP-2 (5 μg, (10) PT+CS+de-N-sulfated heparin (25 μg)+BMP-2 (5 μg). There were 4 replicates for groups (1-3) and 5 replicates for groups (4-10). The doses and ratio of BMP-2 and heparin were based on those used in previous studies [22, 32]. Rats were sacrificed and specimens harvested 8 weeks post-implantation. All samples were assessed with 2D x-rays, μ-CT and histology to assess the extent of bone mineral deposition.

1.10. Surgical Methods

All surgical procedures were performed under aseptic conditions and in strict accordance to the guidelines of A*STAR's Institutional Animal Care and Use Committee. General anesthesia was established by the administration of isoflurane. Two transverse incisions, 1 cm each, were made over each hind limb muscle. Pockets were then created by blunt dissection of the muscle, parallel to the longitudinal-axis of muscle fibers. The specimens were then implanted into these pockets. The incisions were then closed in both the muscle and skin layers. Prophylactic antibiotics (Baytril, 10 mg/kg) and analgesics (Buprenophine, 0.01-0.05 mg/kg) were administered subcutaneously for three days post-operation.

1.11. 2D Radiographic Analysis 2D images of muscle pockets were captured immediately post-operation and at week 8 using an Imaging Radiographic System (MUX-100, Shimadzu). Digital micrographs were subsequently generated from the x-rays.

1.12. 3D μ-CT Analysis

A μ-CT scanner (Skyscan 1076; Skyscan, Belgium) was utilized to scan the harvested specimens (resolution=35 μm; scanning width=68 mm) as per our previous methods [34, 35]. Scanner voltage and current were set to 104 kV and 98 μA respectively. Cone-Beam CT-reconstruction® A Sasov software (Skyscan) was used to process the isotropic slice data and convert into 2D images. Mimics 13.1 software (Materialise, Belgium) was then used to analyze and remodel data in 3D, using the same number of slices and cylindrical region of interest (ROI) for each specimen. The total bone volume within the ROI was quantified by assigning a pre-determined threshold for total bone content. Specimens containing BMP-2, which exhibited zero bone growth via x-ray and μ-CT ($\leq 0.05$ mm$^3$) were excluded from further analysis. Data represents mean±S.E.M. of total bone volume (mm3).

1.13. Histological Evaluation

Specimens were fixed in 10% formalin (neutral buffered) under vacuum for one week. For paraffin histology, specimens were decalcified for two weeks in 30% formic acid at room temperature. The specimens were then processed with a vacuum infiltration processor (Sakura Finetek, Japan) using a 14 h program, followed by dehydration, clearing, and finally embedding in Paraplast® paraffin wax (Thermo Scientific). Paraffin blocks were sectioned longitudinally at 5 μm using a rotary microtome (Leica Microsystems, Germany), and left to dry on positively-charged microscope slides. These slides were subsequently stained with hematoxylin & eosin and modified tetrachrome. Both stains allow for the identification of bone marrow and bone based on its morphology and cellular details. A blue stain and red patches represent osteoid and bone deposition respectively for the modified tetrachrome method. For resin histology, specimens were dehydrated through an ethanol series, followed by processing and embedding in methylmethacrylate. Transverse sections of 5 μm's were cut and stained with von Kossa/MacNeals, for the positive identification of calcified deposits (which stained black). All sections were examined with an Olympus Stereo (SZX12) and upright (BX51) fluorescence microscopes.

1.14. Statistical Methods

All data is represented as the mean±S.D. of at least three independent experiments unless otherwise stated. For statistical analysis, one and two-way analysis of variance (ANOVA) with Tukey's post hoc analysis was performed using Prism 7 software (Graph Pad, San Diego, USA). $P<0.05$ was considered significant. The following symbols were used to indicate p-value range; *$p<0.05$; $p<0.01$; *$p<0.001$; ****$p<0.0001$; ns—not significant ($p>0.05$).

Figure 2:
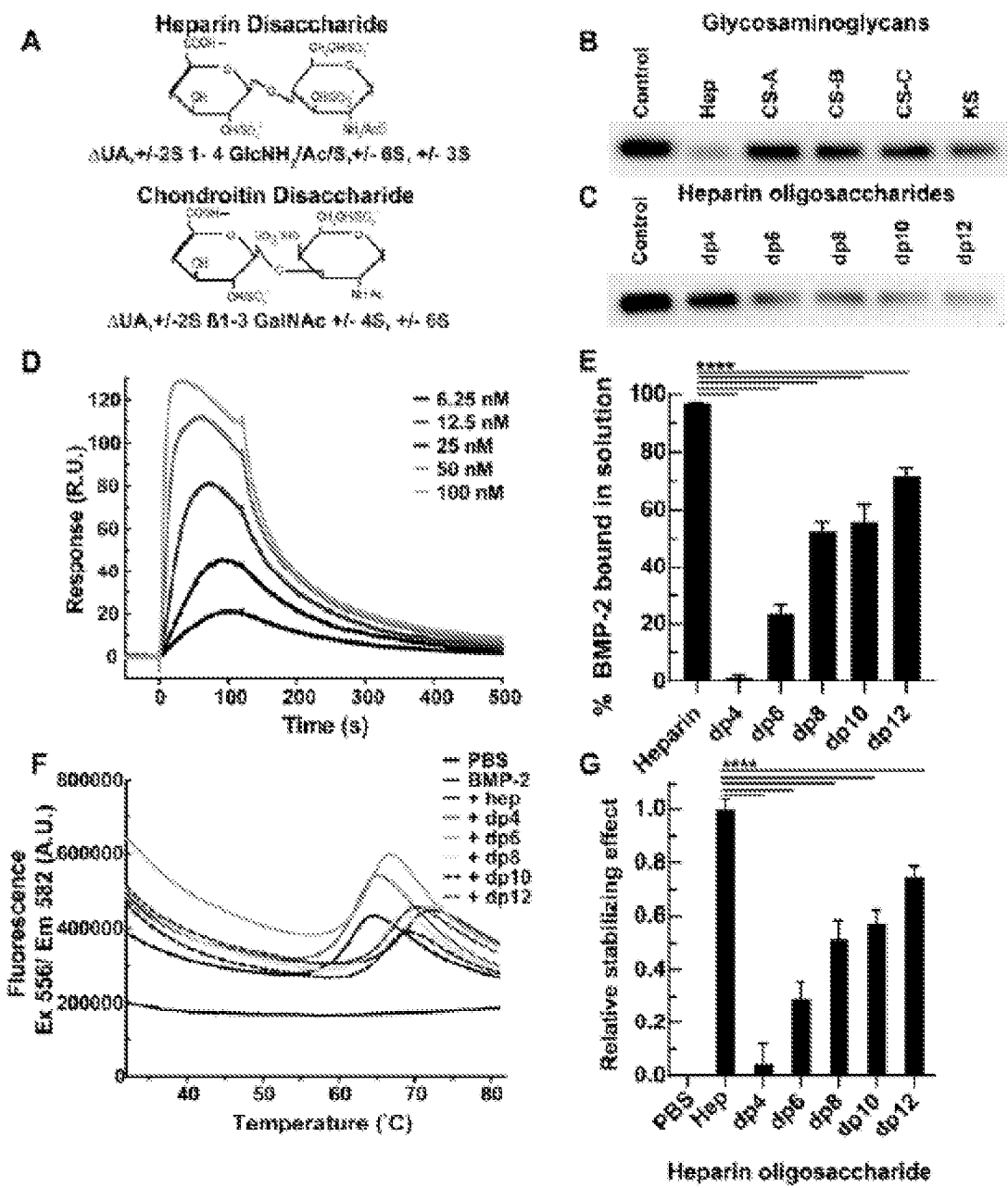
FIG. 2A to 2G. Chain length determines the ability of heparin to bind and stabilize BMP-2. Basic disaccharide structure of heparan sulfate and chondroitin sulfate (A). BMP-2 (20 ng) was incubated with heparin-Sepharose with or without glycosaminoglycans (B) or size defined heparin oligosaccharides (C) and bound BMP-2 detected via Western blot. (D) SPR sensorgram displaying the binding response generated by various concentrations (–6.25 nM, –12.5 nM, –25 nM, –50 nM, –100 nM) of BMP-2 binding to a heparin coated surface. (E) SPR-based competitive binding assays were performed by incubating heparin oligosaccharides (10 µg/mL) with BMP-2 (25 nM) and applying them to a heparin-coated SPR chip. (F, G) Differential scanning fluorimetry was performed by incubating BMP-2 (5 µM) in the presence or absence of heparin oligosaccharides (50 µM; -PBS, -BMP-2 alone, -heparin, -dp4, -dp6, -dp8, --dp10, --dp12). Fluorescence generated from the binding of SYPRO orange dye to the core of denatured BMP-2 was used to 17 determine relative complex stability vs. BMP-2+heparin. All data is representative of (B, C, D, F) or constitutes mean±S.D. (E, G) of three independent experiments. ****$p<0.0001$.

Example 2: Minimum Structural Requirements for BMP-2-Binding of Heparin Oligosaccharides—Results 2.1. Effect of Heparin Oligosaccharide Length on Competitive Binding of BMP-2 to Heparin To assess the minimum saccharide length requirement for binding of heparin to BMP-2, we subjected heparin oligosaccharides (dp4, dp6, dp8, dp10, dp12, dp14, dp16, dp18 or dp20; the structure of a dp2 is illustrated in FIG. 2A) to SPR competitive binding assays. When a range of doses of BMP-2 were applied to a heparin-coated SPR chip, abundant response was observed (FIG. 2B). Pre-incubation with heparin resulted in 97% of the BMP-2 being sequestered in solution, preventing binding to the heparin-coated surface (FIG. 2C). Dp4 were unable to sequester BMP-2 into solution, suggesting they are incapable of preventing BMP-2 from binding the heparin-coated surface. When dp6 and dp8 were pre-incubated with BMP-2 prior to application to the heparin-coated chip, a reduction in R.U. was observed (FIG. 2C). Dp6 and dp8 sequestered 4% and 24% of BMP-2 respectively (FIG. 2C). Dp10, dp12, dp14 and dp16 further sequestered BMP-2 in solution, binding 36%, 61%, 76% and 80% respectively (FIG. 2C). Finally, dp18 and dp20 sequestered 85% and 82% of BMP-2 in solution respectively, quantities comparable to those sequestered by heparin (p>0.05).

2.2. Heparin Oligosaccharides of Increasing Length Enhance the Thermal Stability of BMP-2

We further investigated the interaction between heparin oligosaccharides and BMP-2 by performing DSF, an assay which enabled us to investigate the effect of heparin oligosaccharides on the thermal stability of BMP-2. FIG. 2D displays the shift in peak fluorescence toward a higher temperature upon the addition of oligosaccharides of increasing size (FIG. 2D). FIG. 2E displays the relative increase in the thermal stability of BMP-2 with the addition of native heparin and heparin oligosaccharides ranging between dp4 and dp20. Dp4 and dp8 offered minimal enhancement in BMP-2 thermal stability, whereas dp8 and dp10 enhance BMP-2 thermal stability to half that achieved by native heparin (FIG. 2E). Dp12 offered a further increase in thermal stability over the smaller fragments, and further increases in stability were observed for dp14, dp16 and dp18. Dp20 offered further increases in thermal stability, comparable with native heparin. Statistical analysis using one-way ANOVA revealed that oligosaccharide size had a significant effect on BMP-2 thermal stability (p<0.0001). Further post hoc comparisons between individual groups indicated that the stabilizing effect of dp4-dp18 on BMP-2 was significantly less than that of native heparin (p<0.0001), with only a dp20 offering comparable stability to heparin (p>0.05).

2.3. Size-Exclusion Chromatography of BMP-2 and Heparin Oligosaccharides

Figure 3:
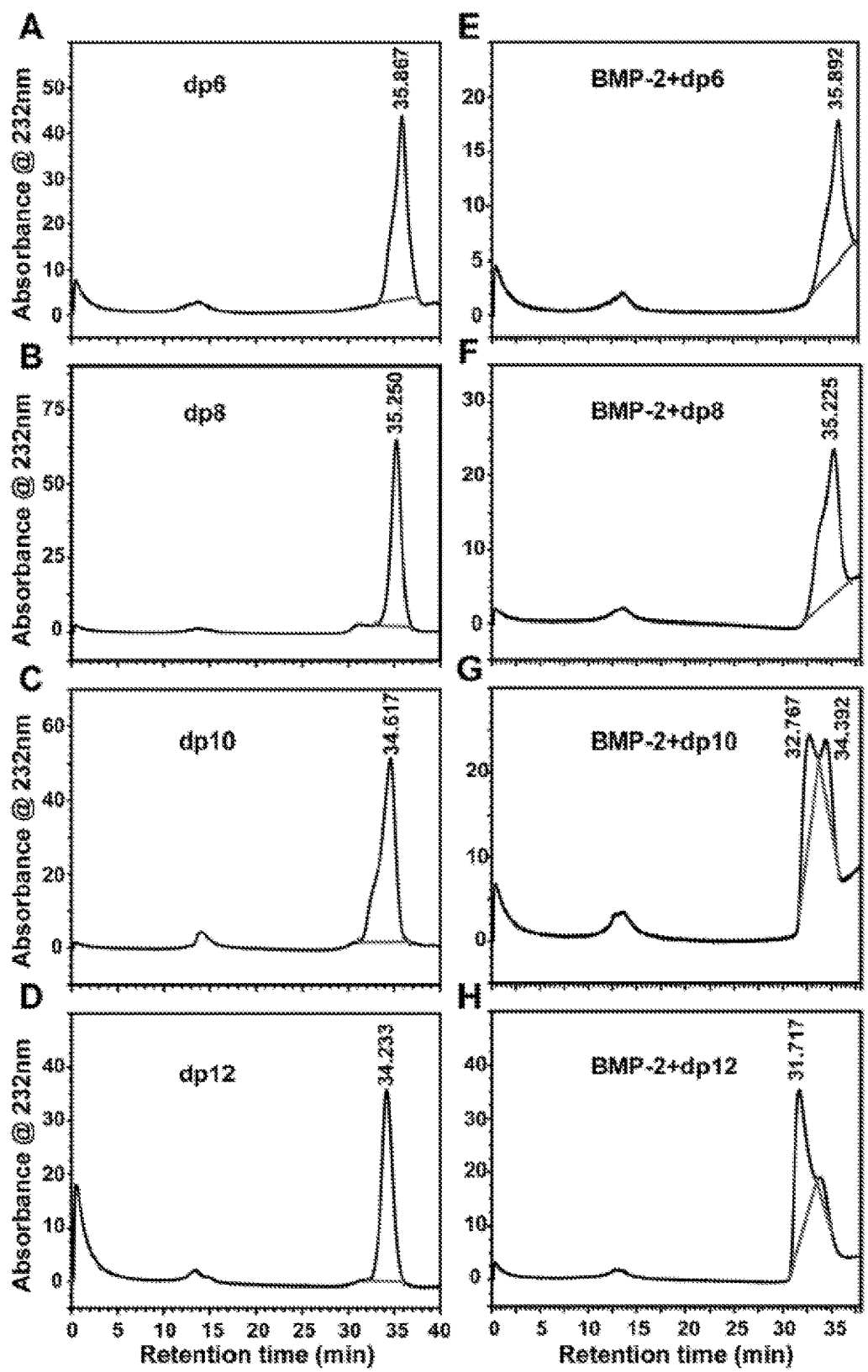
FIG. 3A to 3H. Size-exclusion chromatography of BMP-2 binding to heparin oligosaccharides. (A-D) 25 µM of each heparin oligosaccharides (dp6, dp8, dp10 or dp12) were eluted from a Superdex 200 column detected using absorption at 232 nm. (E-H) 25 µM BMP-2 and 25 µM of each heparin oligosaccharides (dp6, dp8, dp10 or dp12) were eluted from a Superdex 200 column and detected using absorption at 232 nm. Chromatographs are representative of three independent experiments.

We next investigated the ability of oligosaccharides to bind BMP-2 using a size-exclusion chromatographic technique. FIG. 3(A-D) displays the dp6-12 peak elution positions. After incubation of heparin oligosaccharides, it is evident that the elution position of dp6 or dp8 saccharides remained unaffected by BMP-2 (FIG. 3E-F); indicating that minimal binding occurred between BMP-2 and dp6 or dp8 fragments. In contrast, the elution position of the dp10 saccharide was split equally into BMP-2-bound and -unbound peaks (FIG. 3G), again indicating this is the minimal heparin length required for BMP-2 binding. When BMP-2 was incubated with the dp12 preparation, the elution position of the single major peak was significantly shifted (FIG. 3H). These data confirmed that dp10 is the minimal heparin oligosaccharide length required for significant levels of BMP-2 binding, and dp12 for maximal levels. For subsequent in vitro studies, dp4 to dp12 were used.

Figure 4:
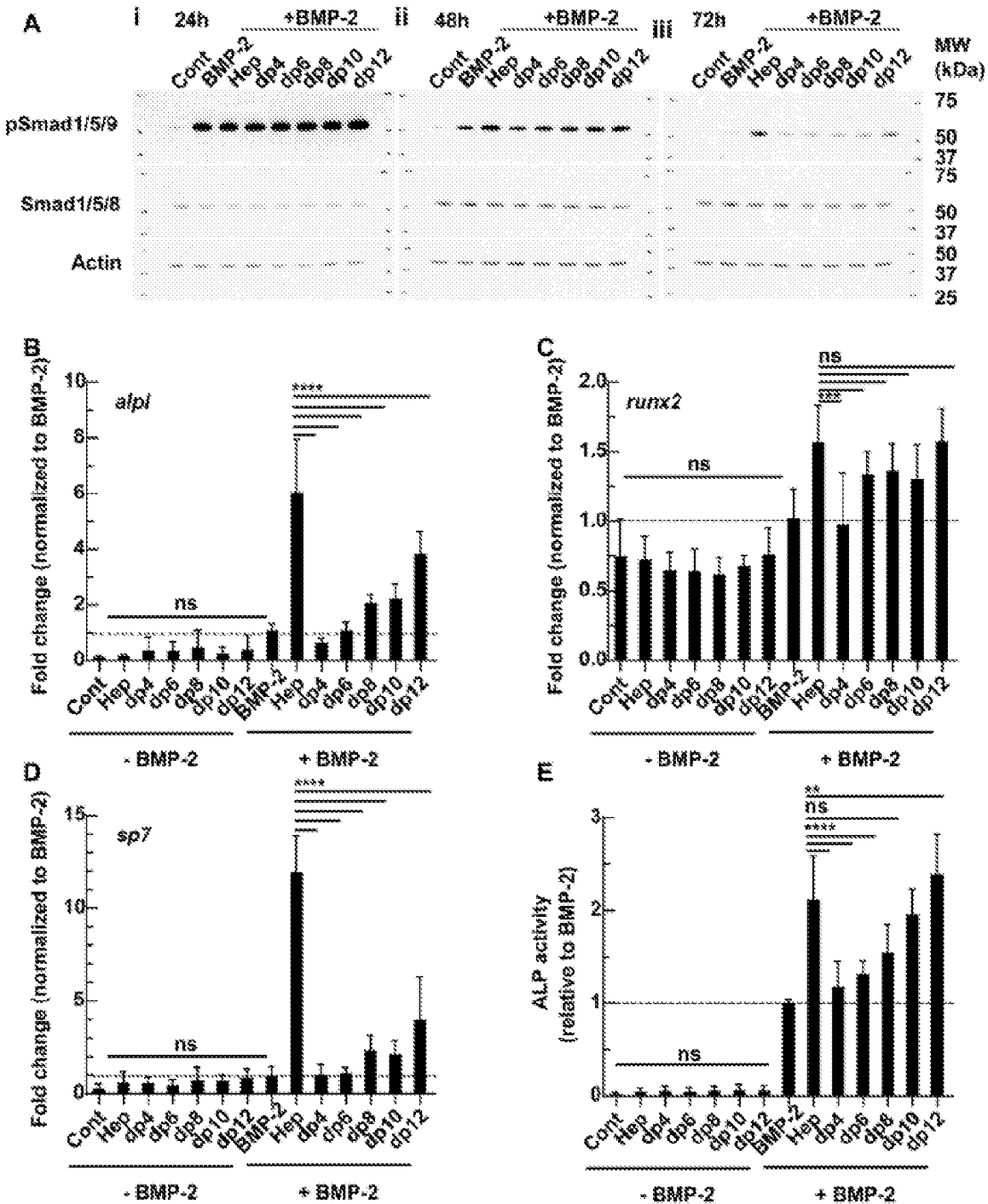
FIG. 4A to 4E. BMP-2-induced Smad 1/5/9 phosphorylation, osteogenic gene transcription and ALP activity with heparin oligosaccharides. (A) C2C12 cells were stimulated with or without BMP-2 (100 ng/mL) and heparin oligosaccharides (dp4, dp6, dp8, dp10, and dp12; 5 µg/mL) for up to 72 h. Smad 1/5/9 phosphorylation was then detected via Western blot. C2C12 cells were stimulated with BMP-2 in the presence or absence of heparin or heparin oligosaccharides for 3 days, after which osteogenic gene transcription (B-D) or ALP activity (E) was determined. Data are represented as the mean±S.D. of three independent experiments. **$p<0.0001$, *$p<0.001$, **$p<0.01$, ns–$p>0.05$.

2.4. Heparin Oligosaccharide Length Influences BMP-2-Induced Signaling and Differentiation of C2C12 Cells We next examined the time course changes induced by BMP-2 and oligosaccharides (dp4-dp12) in the phosphorylation of the specific downstream BMP-2 intracellular effector Smad 1/5/9. In the absence of additional heparin oligosaccharides, the levels of BMP-2-induced Smad 1/5/9 phosphorylation were detectable at 24 and 48 h; after 72 h, Smad 1/5/9 phosphorylation was no longer detectable in cultures exposed to BMP-2 alone (FIG. 4Ai-iii). Smad 1/5/9 phosphorylation levels were similar across all treatment groups at 24 and 48 h (FIG. 4Ai-ii). At 72 h, Smad 1/5/9 phosphorylation had decreased progressively in cultures treated with shorter oligosaccharides (dp4, dp6 or dp8; FIG. 4Aiii). Cultures treated with heparin or dp12 fragments displayed the highest levels of Smad 1/5/9 phosphorylation (FIG. 4Aiii). These data confirm that oligosaccharides ≥dp10 in length prolong and maintain BMP-2-induced Smad 1/5/9 phosphorylation. We next compared the bioactivity of heparin oligosaccharides by assaying BMP-2-induced upregulation of osteogenic gene transcripts and ALP activity in C2C12 myoblast cells. We chose to assess changes in transcript level of alpl, runx2 and sp7, as all are markers of osteogenic differentiation. Additionally we chose to assess ALP activity as ALP is a key marker of osteogenic differentiation. Alone, heparin and heparin oligosaccharides did not induce expression of osteogenic genes alpl, sp7 and runx2, or ALP activity (FIG. 4B-E). However, when cells were exposed to 100 ng/ml of BMP-2, in the presence of heparin, a rapid induction of osteogenic gene transcription and ALP activity was observed (FIG. 4B-E). Dp4 and dp6 failed to substantially upregulate BMP-2-induced gene transcription or enhance ALP activity over BMP-2 alone (FIG. 4B-E). Dp8 upregulated gene transcription and enhanced ALP activity, but to a lesser extent than native heparin (FIG. 4B-E). However, dp10 enhanced BMP-2-induced ALP activity to the levels of native heparin (FIG. 4E, p>0.05) and dp12 are capable of significantly enhancing BMP-2-induced ALP activity over native heparin (p<0.01). Dp12s also enhanced osteogenic gene transcription, but not to the level of native heparin in the case of Alpl and Sp7 (FIG. 4B, D). Thus the minimum oligosaccharide length required for maintenance of BMP-2-induced transcription of osteogenic genes and enhancement of ALP activity is a dp12.

2.5. Selectively Desulfated Heparin Interactions with BMP-2

Figure 5:
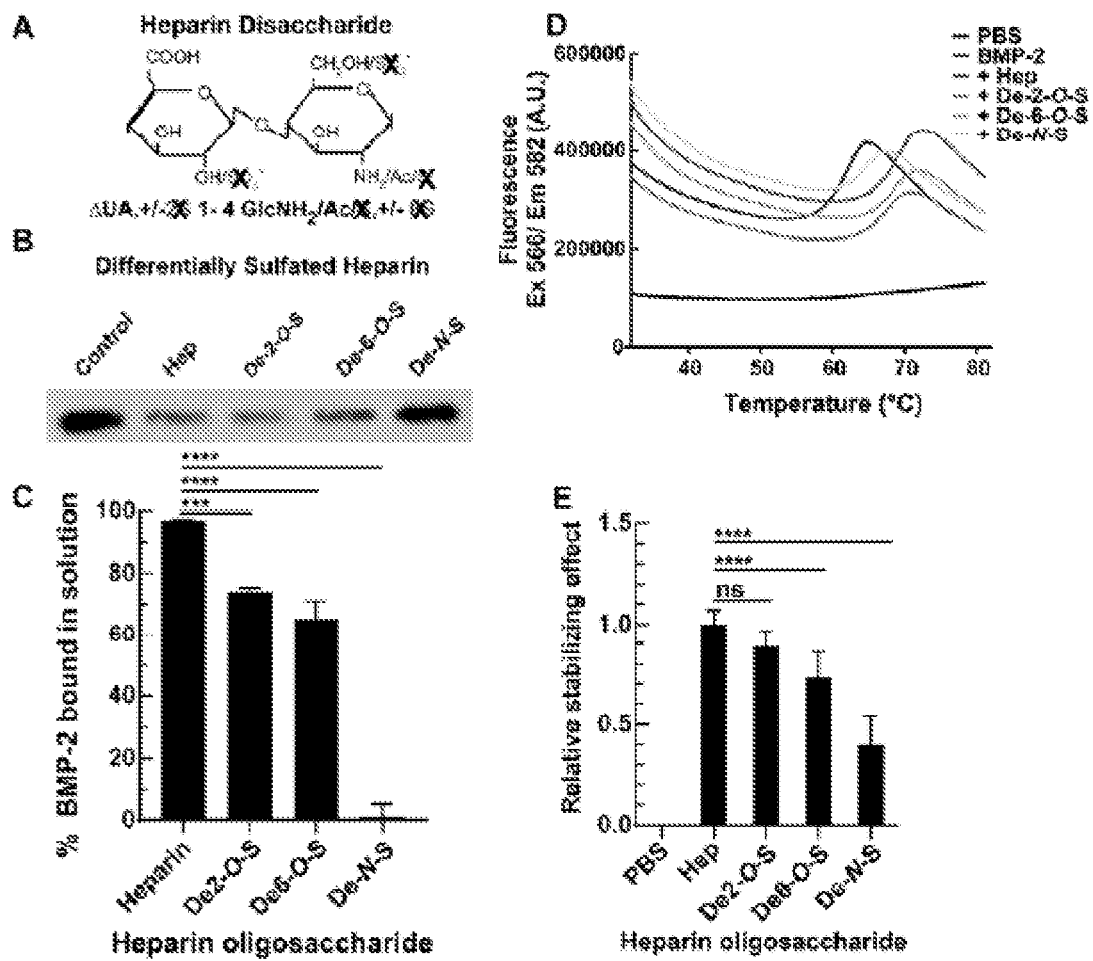
FIG. 5A to 5E. BMP-2 binding and thermal stability by desulfated heparins. (A) The structure of the main repeating disaccharide unit in heparin/HS chains. (B) Competition of BMP-2 (20 ng) binding to heparin Sepharose beads. (C) SPR-based competitive binding assays were performed by incubating selectively desulfated heparins (10 µg/mL) with BMP-2 (25 nM) and applying them to a heparin-coated SPR chip. (D-E) Differential scanning fluorimetry was performed by incubating BMP-2 (5 µM) with or without selectively desulfated heparins (50 µM) and SYPRO orange dye at increasing temperature (-PBS, -BMP-2 alone, -heparin, -de-2-O-sulfated, -de-6-O-sulfated, -de-N-sulfated). Fluorescence generated from the binding of SYPRO orange dye to the core of denatured BMP-2 was used to determine relative complex stability vs. BMP-2+heparin. Data is representative of (B, D) or constitutes mean±S.D. (C, E) of three independent experiments. ****$p<0.0001$; ns–$p>0.05$.

The structure of the disaccharide units in heparin is depicted in FIG. 5A. Heparin chains contain an abundance of N-, 2-O-, and 6-O-sulfate groups, as well as the rarer 3-O-sulfate group, and these substitutions (when organized into specific sequences or domains) are responsible for interaction with heparin/ HS-binding proteins. To determine the importance of specific sulfate groups of heparin/HS chains in the binding of BMP-2, we performed SPR competitive binding experiments to ascertain how well selectively desulfated heparins can out-compete surface heparin for the binding of BMP-2. Heparin and de-2-O-sulfated heparin sequestered a substantial amount of BMP-2 into solution (73%) in SPR competition assays (FIG. 5B). As observed in the GAG binding plate assay, de-6-O-sulfated heparin displayed a marginally lower affinity to BMP-2, sequestering 63% of BMP-2 in solution (FIG. 5B). Finally, de-N-sulfated heparin was unable to bind and sequester any BMP-2 into solution, however, re-N-acetylation of the free amine group rescued BMP-2 binding, resulting in 51% of BMP-2 being sequestered into solution (FIG. 5B). These data indicate a hierarchy of necessity, wherein N-sulfation is essential for BMP-2 binding, with 6-O-sulfation partially contributing and 2-O-sulfation only minimally.

2.6. Effect of Selectively Desulfated Heparins on the Thermal Stability of BMP-2

We further investigated the interactions of selectively desulfated heparins and BMP-2 by using DSF. Pre-incubating BMP-2 with selectively desulfated heparins resulted in a decrease in the melting temperature of BMP-2 compared to that with heparin, evident by a shift in peak fluorescence to a lower temperature (FIG. 5C). The loss of 2-O and 6-O-sulfation resulted in a ~10% and ~20% reduction in the thermal stabilizing effect of heparin, respectively (FIG. 5D). Loss of N-sulfation further reduced the thermal stabilizing effect of heparin, to ~33% of that of native heparin (FIG. 5D). Re—N-acetylation of de-N-sulfated heparin resulted in an improvement in the thermal stabilizing effect, from 33% to 71% (FIG. 5D). Statistical analysis via one-way ANOVA revealed that sulfation contributes significantly to the thermal stabilizing effect of heparin toward BMP-2 (FIG. 5D;

**p<0.0001). The loss of 6-O-sulfation results in significant reduction in stabilizing effect (*p<0.001), however the of 2-O-sulfation did not result in a significant reduction in the stabilizing effect of heparin (ns–p>0.05). The loss of N-sulfation resulted in a significant reduction in stabilizing effect (**p<0.0001); subsequent re-N-acetylation improved the stabilizing effect over de-N-sulfated species, but to a level that is still significantly lower than that of native heparin (**p<0.0001). These data once again confirm a hierarchy of importance with regards to sulfation. N-sulfation plays an essential role in the thermal stabilizing effect of heparin on BMP-2, while 6-O-sulfation offers a partial contribution and 2-O-sulfation offering a minimal contribution.

Figure 6:
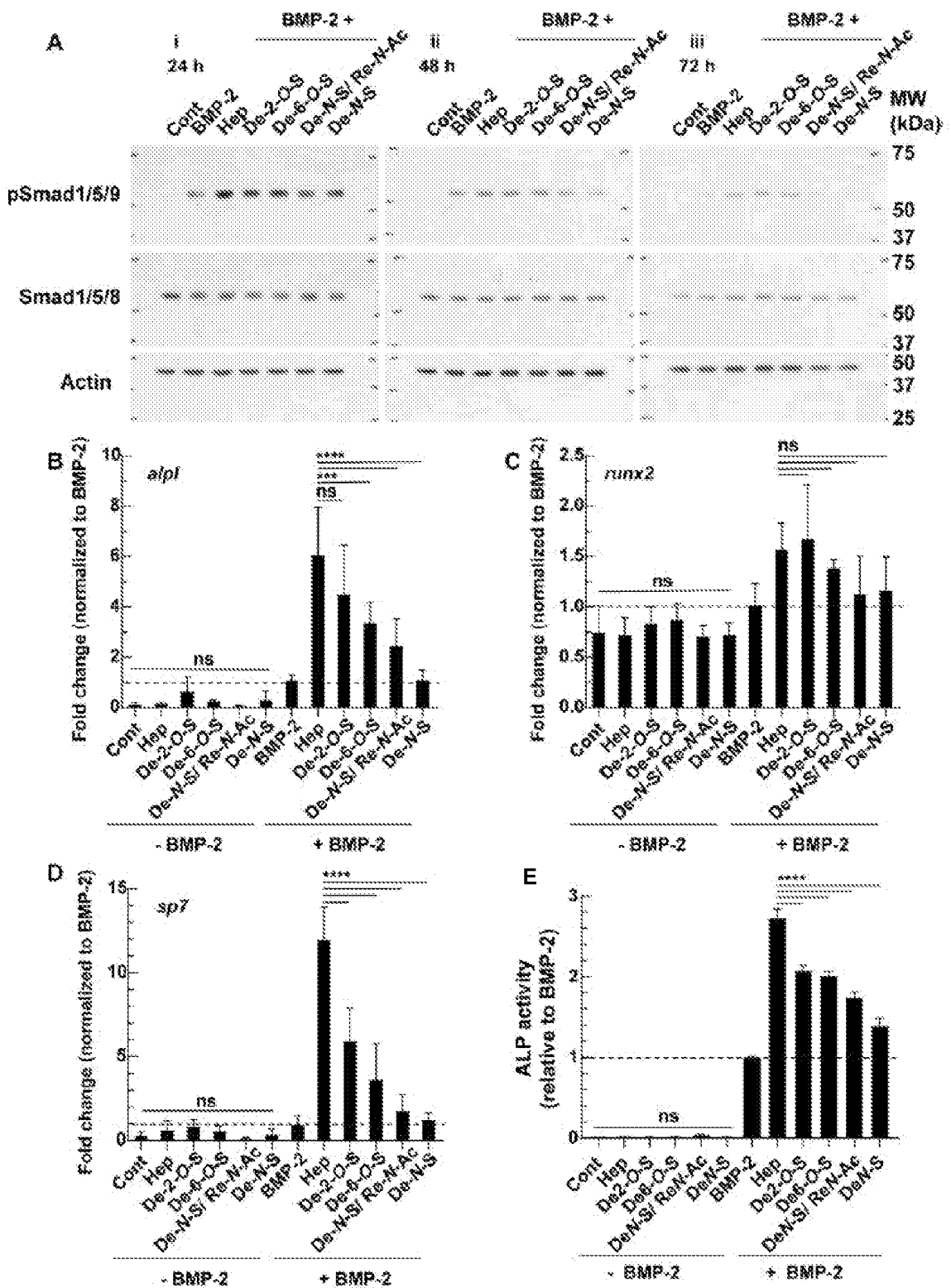
FIG. 6A to 6E. BMP-2-induced Smad 1/5/9 phosphorylation, transcription of osteogenic genes and ALP activity with selectively desulfated heparins. (A) C2C12 cells were stimulated with or without BMP-2 (100 ng/mL) and heparin or specific desulfated heparins (5 µg/mL) for up to 72 h. Smad 1/5/9 phosphorylation was then detected via Western blot. (B-E) C2C12 cells were stimulated with or without BMP-2 (100 ng/mL) in the presence or absence of heparin or desulfated heparin (5 µg/mL) and cultured for 3 days, after which osteogenic gene transcription (B-D) or ALP activity (E) were determined. Data are represented as the mean±S.D. of three independent experiments. **$p<0.0001$, *$p<0.001$, ns–$p>0.05$.

2.7. Effect of Selectively Desulfated Heparins on BMP-2-Induced Osteogenic Gene Transcription and ALP Activity We next studied the importance of specific sulfate groups within heparin/HS chains in BMP-2-induced Smad 1/5/9 phosphorylation, transcription of osteogenic genes and enhancement of ALP activity assay. Similar to observations with sized heparin oligosaccharides, phosphorylation levels of Smad 1/5/9 were not affected within 24 h by heparin and selectively desulfated heparins (FIG. 6Ai); however, at 48 h, the levels decreased in cultures treated with de-N-sulfated or de-N-sulfated/re-N-acetylated heparins (FIG. 6Aii). After 72 h, cultures treated with heparin, de-2-O-sulfated or de-6-O-sulfated heparin displayed the highest levels of Smad 1/5/9 phosphorylation (FIG. 6Aiii). Smad 1/5/9 phosphorylation was barely detectable in cultures treated with BMP-2 alone or BMP-2 with de-N-sulfated and de-N-sulfated/re-N-acetylated heparins after 72 h (FIG. 6Aiii). Heparin and selectively de-sulfated heparins alone had no effect on gene transcription (FIG. 6B-D) or ALP activity in C2C12 cells (FIG. 6E). However, when cells were treated with a combination of BMP-2 (100 ng/ml) and heparin (5 µg/ml), the induction of alpl, sp7 and runx2 transcription and ALP activity was greatly enhanced (FIG. 6B-E). De-2-O-sulfation of heparin did not significantly affect the enhancement of alpl and runx2 transcription (FIG. 6B, C; p>0.05), but resulted in a significant reduction in sp7 transcripts and ALP activity (FIG. 6D, E; p<0.0001). De-6-O-sulfation or de-N-sulfation and subsequent re-N-acetylation of heparin significantly reduced BMP-2-induced alpl and sp7 transcription and ALP activity (FIG. 6B-E); p<0.0001). These data clearly indicate the essential role of N-sulfation in enhancing BMP-2-induced Smad 1/5/9 phosphorylation, osteogenic gene transcription and ALP activity in C2C12 cells, more so than 6-O- and especially 2-O-sulfation.

Figure 7:
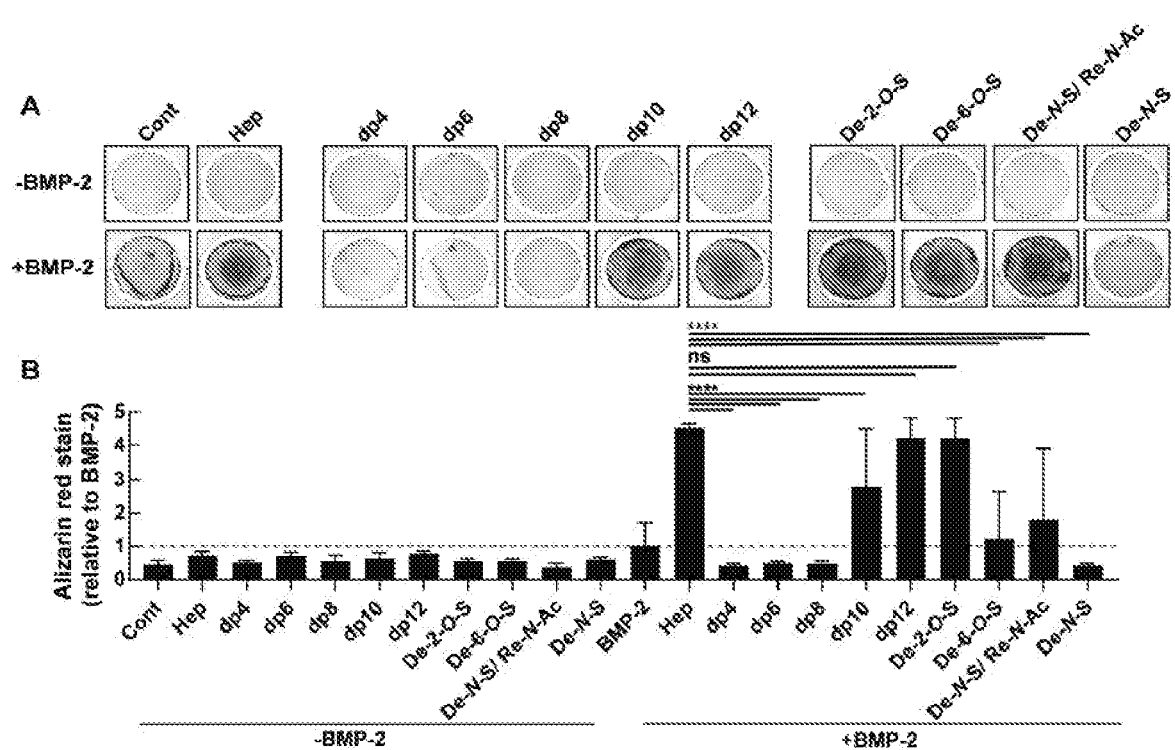
FIG. 7A to 7B. BMP-2-induced osteogenic differentiation and mineralization with heparin oligosaccharides and selectively desulfated heparins. C2C12 cells were stimulated with or without BMP-2 (100 ng/mL) and heparin, heparin oligosaccharides or specific desulfated heparins (5 µg/mL) for 12 days. (A) Cells were stained with Alizarin red to detect the presence of calcium. (B) Alizarin red was extracted and quantified using spectrophotometry (absorbance at 405 nm) and normalized to the BMP-2 alone treatment group. Data is representative of (A) or represented as (B) the mean±S.D. of three independent experiments. ****$p<0.0001$, ns–$p>0.05$.

2.8. Effect of Heparin Oligosaccharides on BMP-2-Induced Osteogenic Differentiation and Mineralization We further investigated the length and sulfation requirements within heparin chains by employing an osteogenic differentiation assay over the course of 12 days. We observed that BMP-2 alone (100 ng/mL) was not sufficient to induce mineralization in C2C12 cells, as indicated by calcium deposition detected by Alizarin red stain (FIG. 7A-B). The addition of heparin and BMP-2 lead to extensive mineralization, as evident from the presence of Alizarin red staining (FIG. 7A-B). Addition of heparin oligosaccharides dp4, dp6 and dp8 did not enhance mineralization in the presence or absence of BMP-2 (FIG. 7A-B). Addition of heparin dp10 with BMP-2 increased mineralization, although not to the level of heparin (p<0.0001), whilst addition of heparin dp12 enhanced mineralization to similar levels of native heparin (ns; p>0.05; FIG. 7A-B). De-N-sulfated heparin was incapable of enhancing mineralization, and de-6-O-sulfated heparin only minimally enhanced mineralization (FIG. 7A-B). De-2-O-sulfated heparin enhanced mineralization to the same extent as native heparin (ns; p>0.05; FIG. 7A-B). Re—N-acetylation of de-N-sulfated heparin partially rescued the ability of heparin to enhance BMP-2-mediated mineralization, but not to the level of de-2-O-sulfated heparin (FIG. 7A). These data indicate that a minimum length of a dp10 (optimally a dp12) and N-sulfation (optimally N- and 6-O-sulfation) are required for heparin to enhance BMP-2-mediated osteogenic differentiation in C2C12 cells.

2.9. Ectopic Bone Formation

Figure 8:
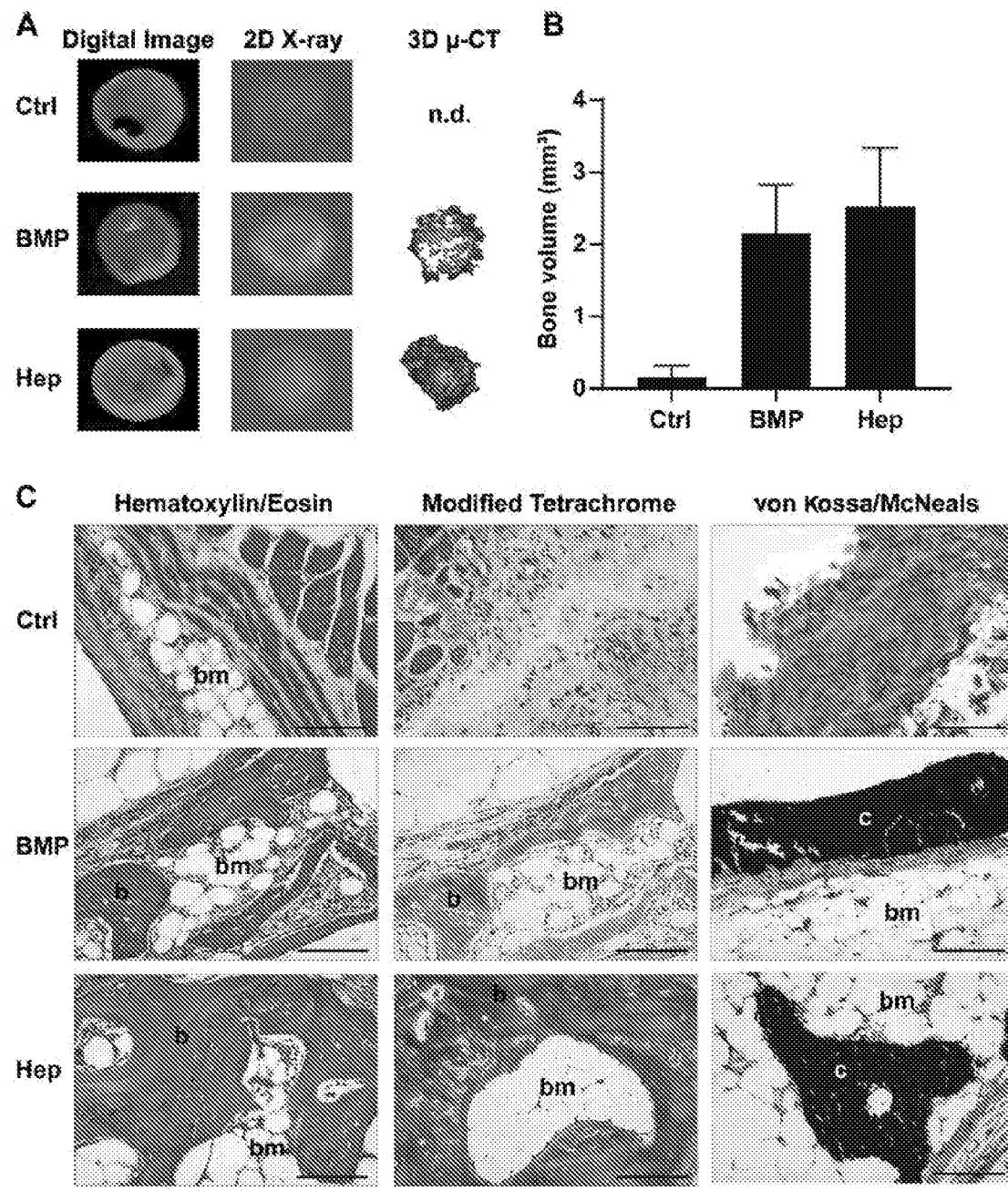
FIG. 8A to 8C. Establishment of controls for the rat ectopic bone formation assay. (A) Representative digital image, 2D x-rays and 3D µ-CT micrographs of samples harvested from the hind limb muscle of rats. The treatments were collagen sponges alone (Ctrl; n=4); or with 5 µg BMP-2 (BMP; n=4); or with 5 µg BMP-2+25 µg heparin (Hep; n=4). (B) The bone volume measurements (mm3) for the respective samples as determined by µ-CT analyses. Results are expressed as mean±S.E.M. (C) Representative histological sections showing the absence/presence of calcified bone matrix in the harvested samples. Staining consisted of Hematoxylin/Eosin, Modified Tetrachrome (blue: osteoid, red: bone) and von Kossa/McNeals (black: calcified deposits). BM: Bone marrow, B: Bone, C: Calcified matrix, scale bars-100 µm. (For interpretation of the references to colour in this figure legend, the reader is referred to the Web version of this article.)

The comprehensive in vitro data strongly suggests that lengths of at least dp10 containing essential N-sulfated motifs are crucial for the biological activation of BMP-2 by heparin. To widen the validity of these observations, selected oligosaccharides were next tested in an in vivo rat ectopic bone-forming model. All rats survived the surgeries and recovered uneventfully. PCL tubes were used in the study to allow for straightforward implant retrieval and did not contribute to any bone formation (data not shown). FIG. 8 shows the combined results for the positive and negative controls. The digital, 2D x-ray and 3D µ-CT micrographs correlate well and demonstrated increased amounts of mineralization when BMP-2 was present in the implant (Ctrl, BMP and Hep; FIG. 8A). Bone volume measurements revealed a similar trend (FIG. 8B). BMP-2 alone resulted in ~16-fold increase in bone volume compared to control (Ctrl), while treatment with BMP-2 complexed with native heparin resulted in ~0.2-fold increase over BMP-2 alone. One sample from the BMP-2/heparin group displayed no bone formation via x-ray and µ-CT, therefore was excluded from further analysis. The difference between BMP-2 and BMP-2/heparin groups is comparable to that observed in a previous study using a similar ectopic model [49]. Paraffin and resin histology were both performed to confirm the presence of bone-like tissue. No bone was detected in controls, unlike the BMP-2 and BMP-2/heparin treatments, which resulted in the infiltration of bone marrow and the deposition of a calcified bone matrix (with osteocytes clearly visible within lacunae) as observed in H&E-, modified tetrachrome- and von Kossa/McNeals-stained sections (FIG. 8C).

Figure 9:
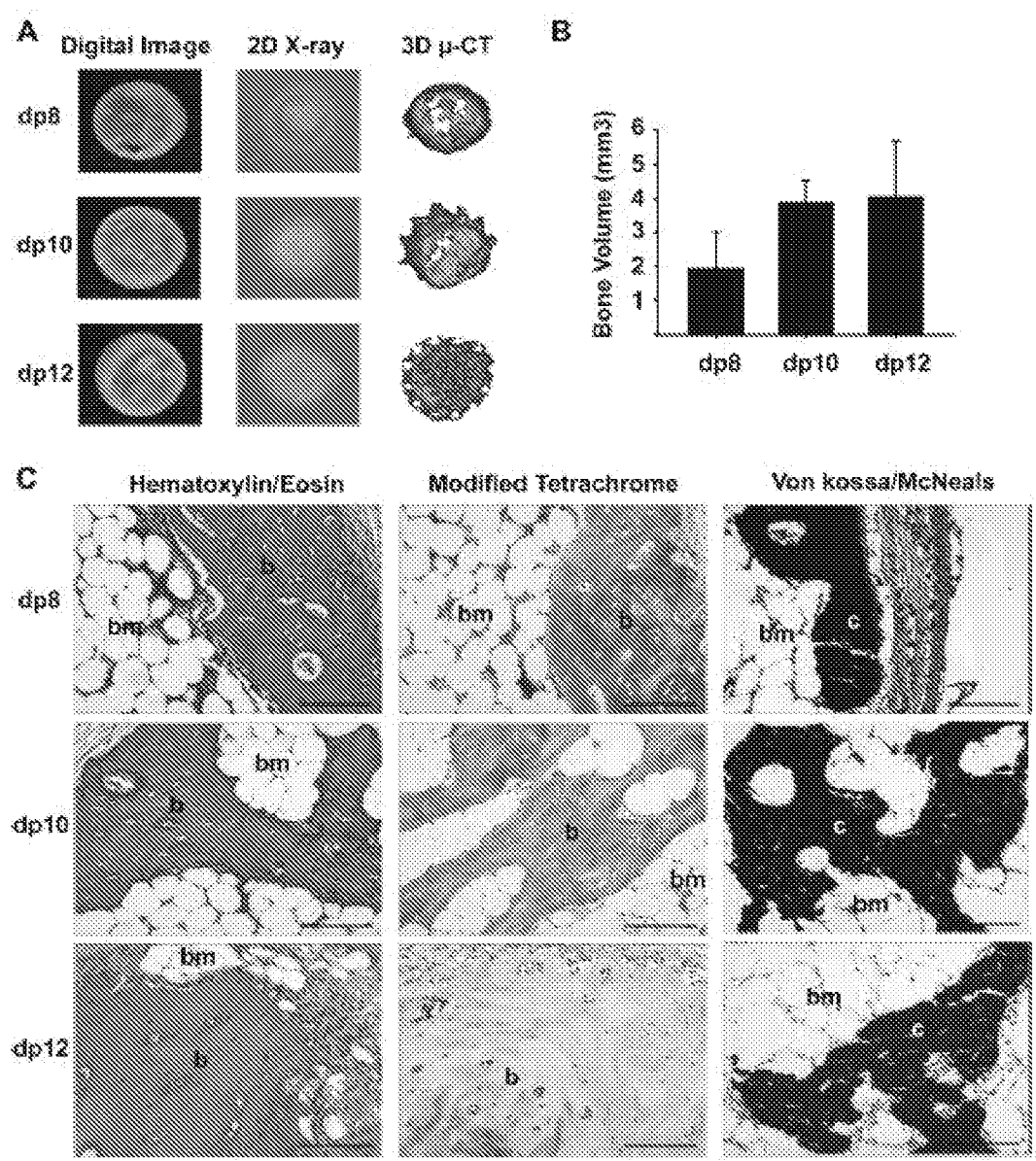
FIG. 9A to 9C. The assessment of dps8, 10 and 12 in a rat ectopic bone formation assay. (A) Representative digital images, 2D x-rays and 3D µ-CT micrographs of samples harvested from the hind limb muscle of rats. The treatments were collagen sponges with 5 µg BMP-2 and 25 µg of dps8 (n=4), 10 (n=4) or 12 (n=5). (B) The bone volume measurements (mm3) for the respective samples as determined by µ-CT analyses (dashed line represents bone volume for heparin treatment group). Results are expressed as mean±S.E.M. (C) Representative histological sections showing the presence of calcified bone matrix in the samples. Staining consisted of Hematoxylin/Eosin, Modified Tetrachrome (blue: osteoid, red: bone) and von Kossa/McNeals (black: calcified deposits). BM: Bone marrow, B: Bone, C: Calcified matrix, scale bars-100 µm.

Once the controls were established, the in vivo performance of BMP-2 complexed with dp8, 10 and 12 saccharides were investigated (FIG. 9). Once again there was good correlation between the digital, 2D x-ray and 3D µ-CT micrographs (FIG. 9A). One sample from each of the dp8 and dp10 groups displayed no bone formation via x-ray and µ-CT, therefore they were excluded from further analysis. The dp8 treatment resulted in less bone deposition than dps 10 and 12. This trend was supported by bone volume measurements that revealed a ~1.7-fold increase with dp12 as compared with dp8 (FIG. 9B). Histological sectioning confirmed the deposition of a calcified bone matrix; this was interspersed within the bone marrow for all three groups, with the dp8 group displaying the least overall amount of bone tissue (FIG. 9C). These data indicate a clear trend that increasing chain length enhances BMP-2-induced bone formation in vivo.

Figure 10:
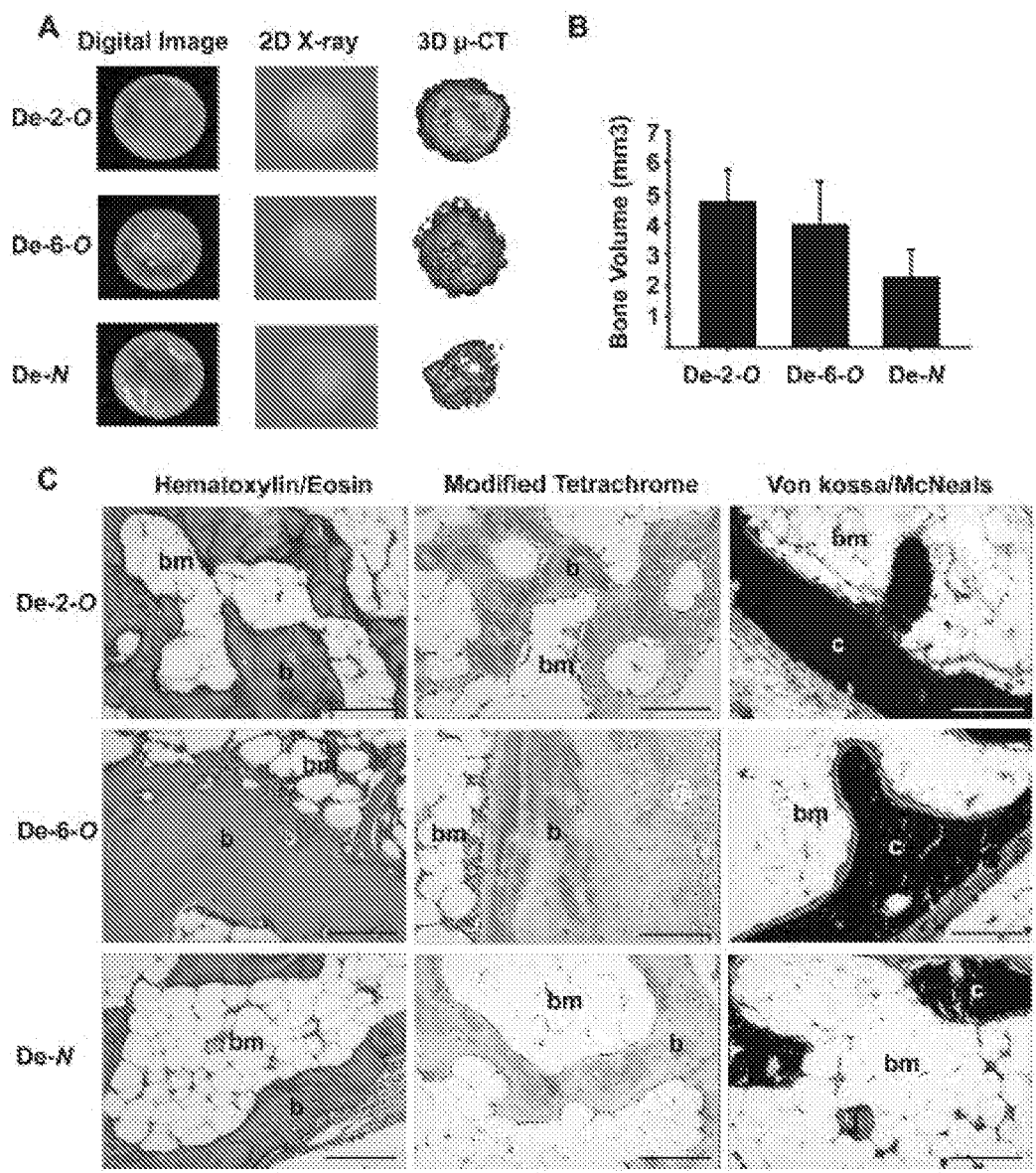
FIG. 10A to 10C. The assessment of de-2-O-, de-6-O- and de-N-sulfated heparins in a rat ectopic bone formation assay. (A) Representative digital image, 2D x-rays and 3D µ-CT micrographs of samples harvested from the hind limb muscle of rats. The treatments were collagen sponges with 5 µg BMP-2 and 25 µg of de-2-O- (n=4), de-6-O- (n=4) or de-N-sulfated (n=5) heparins. (B) The bone volume measurements (mm3) for the respective samples as determined by µ-CT analyses (dashed line represents bone volume for heparin treatment group). Results are expressed as mean±S.E.M. (C) Representative histological sections showing the presence of calcified bone matrix in the harvested samples. Staining consisted of Hematoxylin/Eosin, Modified Tetrachrome (blue: osteoid, red: bone) and von Kossa/McNeals (black: calcified deposits). BM: Bone marrow, B: Bone, C: Calcified matrix, scale bars-100 μm.

Finally, we contrasted the in vivo effectiveness of BMP-2 complexed with de-2-O-, de-6-O- and de-N-sulfated heparins (FIG. 10). One sample from each of the de-2-O—S and de-6-O—S groups displayed no bone formation via x-ray and µ-CT, therefore they were excluded from further analysis. The digital, 2D x-ray and 3D µ-CT micrographs showed that de-2-O- and de-6-O-sulfated oligosaccharides resulted in enhanced mineral deposition compared to those de-N- sulfated (FIG. 10A). This observation corresponded to bone volume measurements, where the former displayed an increase in bone volume compared to the latter (FIG. 10B). Meanwhile, the loss of 2-O- and 6-O-sulfate groups did not affect the in vivo efficacy of these heparin variants, as indicated by comparable bone volume measurements between the two groups. Histological sections mirrored this trend, and although calcified bone matrices with bone marrow elements were observed for all treatments, the de-N-sulfated group had noticeably reduced amounts of new bone tissue (FIG. 10C).

Example 3: Minimum Structural Requirements for BMP-2-Binding of Heparin Oligosaccharides—Discussion Information regarding the precise structure and composition of the bioactive domains of HS remains essential if reliable HS-based therapeutics are to be formulated. This knowledge, detailing the structural and functional relationships between HS and proteins, may also aid in the eventual creation of synthetic HS analogues, which could eventually negate the requirement for animal-derived products. The work here describes our initial attempts to more closely define the essential elements of BMP-2-activating heparin/HS domains, as we have previously with TGF-β1 [36]. The results of this study indicate a minimal chain length of ten monosaccharides (dp10, decasaccharide), and the central importance of N-sulfation in the binding of BMP-2 and potentiation of its biological activity, both in vitro and in vivo. These data regarding sulfation are in agreement with previous studies; these indicated a hierarchy of importance in heparin sulfation for effective binding of BMP-2 and potentiation of its biological activity [37, 38]. Specifically, data presented in these studies and the current study highlight the importance of N-sulfation. Such information on specific requirements for size and sulfation may in turn be incorporated into artificial HS analogues, as synthetic techniques begin to mature [39, 40].

Figure 11:
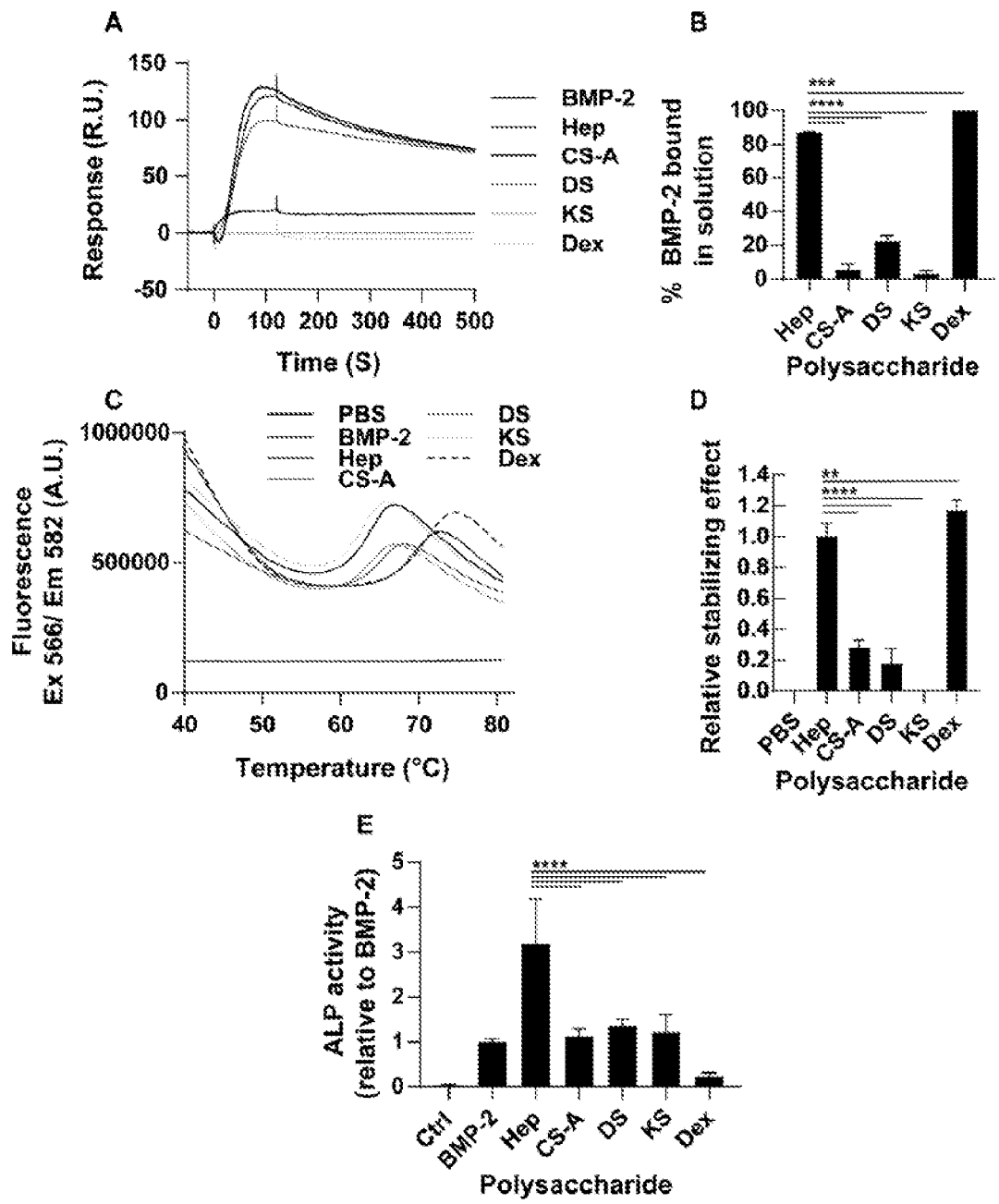
FIG. 11A to 11E. Binding, stabilization and activation of BMP-2 by other sulphated polysaccharides. (A) Representative SPR sensorgrams displaying the binding response generated by various sulfated polysaccharides (10 μg/mL) pre-incubated with BMP-2 (25 nM) and applied to a heparin-derivitised surface. (B) Normalized SPR data derived from (A) indicating the percentage of BMP-2 sequestered into solution by various sulphated polysaccharides. (C) Differential scanning fluorimetry was performed by incubating BMP-2 (5 μM) in the presence or absence of various sulfated polysaccharides (50 μM). (D) Fluorescence generated from the binding of SYPRO orange dye to the core of denatured BMP-2 was used to determine relative complex stability vs. BMP-2+heparin. (E) C2C12 cells were treated with BMP-2 (100 ng/mL) with or without various sulphated polysaccharides (5 μg/mL) for 3 days, after which protein was extracted and ALP activity was assessed. All data is representative of (A, C) or constitutes mean±S.D. (B, D-E) of three independent experiments. $p<0.01$, *$p<0.001$, ****$p<0.0001$.

Here we first performed a competition assay to more systematically determine the interaction between BMP-2 and various GAG subclasses. BMP-2 has been previously reported to strongly interact with heparin and HS GAGs. In our previous study, we observed little or no binding of BMP-2 to CS-A, CS-C, CS-B (dermatan sulfate) or keratan sulfate (KS) [34]. Indeed, we further confirmed that CS-A, DS and KS bound little BMP-2 and did not enhance BMP-2-mediated ALP activity in C2C12 cells (FIG. 11). Moreover, dextran sulfate, a large and highly charged branching polymer was able to bind BMP-2 with high affinity, but inhibited BMP-2 bioactivity in vitro (FIG. 11). Previous studies have indicated that BMP-7 and FGF-1 interact with heparin and HS, but not CS, whereas FGF-2 can bind heparin and CS-E polysaccharides with similar binding affinities [17, 41].

A number of heparin oligosaccharides of defined size were employed to determine the importance of chain length on BMP-2 binding by SPR competition and size-exclusion chromatography assays. The results demonstrated that heparin fragments of 3-4 disaccharides displayed a limited ability to bind BMP-2, and that binding gradually increased through dp6 and dp8. Longer oligosaccharides, such as dp10 and dp12 displayed high binding to BMP-2, but dp18 provided maximal binding, equivalent to that observed with heparin. Size-exclusion chromatography results confirmed the data acquired from SPR competition assays; dp12 bound large amounts of BMP-2. We additionally performed DSF assays to establish the importance of oligosaccharide length on the thermal stability of BMP-2. These data revealed that increasing chain length resulted in increased thermal stability of BMP-2, with a dp12 offering a substantial increase in thermal stability over BMP-2 alone and a dp20 offering thermal stability equivalent to that of heparin. Together, these data demonstrate a minimal requirement of a dp10, optimally a dp12, and maximally a dp16 for the binding of heparin to BMP-2.

Key experiments have firmly established that a particular 3-O-pentasaccharide within heparin is the minimal size required for antithrombin III binding and activity [28, 42-44]. In contrast, a dp8 was the shortest heparin fragment that could subtend FGF-1 and FGF-2 binding [45, 46], although dp10s were required for optimum proliferative activity [47, 48]. Similarly, the minimum size requirement for FGF-7 and FGF-10 binding to dermatan sulfate is a dp10, although larger oligosaccharides (dps14-20) are required for optimum activity [49, 50]. In addition, we have previously confirmed that oligosaccharides of dp18 and above are required for optimal binding of TGF-β1; furthermore oligosaccharides of dp14 and above promote TGF-β1-induced biological activity in human mesenchymal stem cells (MSCs) [36].

Previous studies have demonstrated that heparin is capable of enhancing BMP-2-induced osteogenic differentiation in C2C12 myoblasts in vitro [21]. Our data demonstrates that oligosaccharides of dp10 and above were able to support this conversion, as evident by increases in osteogenic gene transcription, enhancement in ALP activity and induction of mineralization. Most notably, the animal studies confirmed the in vitro results, demonstrating that increasing chain oligosaccharide length markedly enhanced BMP-2-mediated bone formation in vivo.

Figure 12:
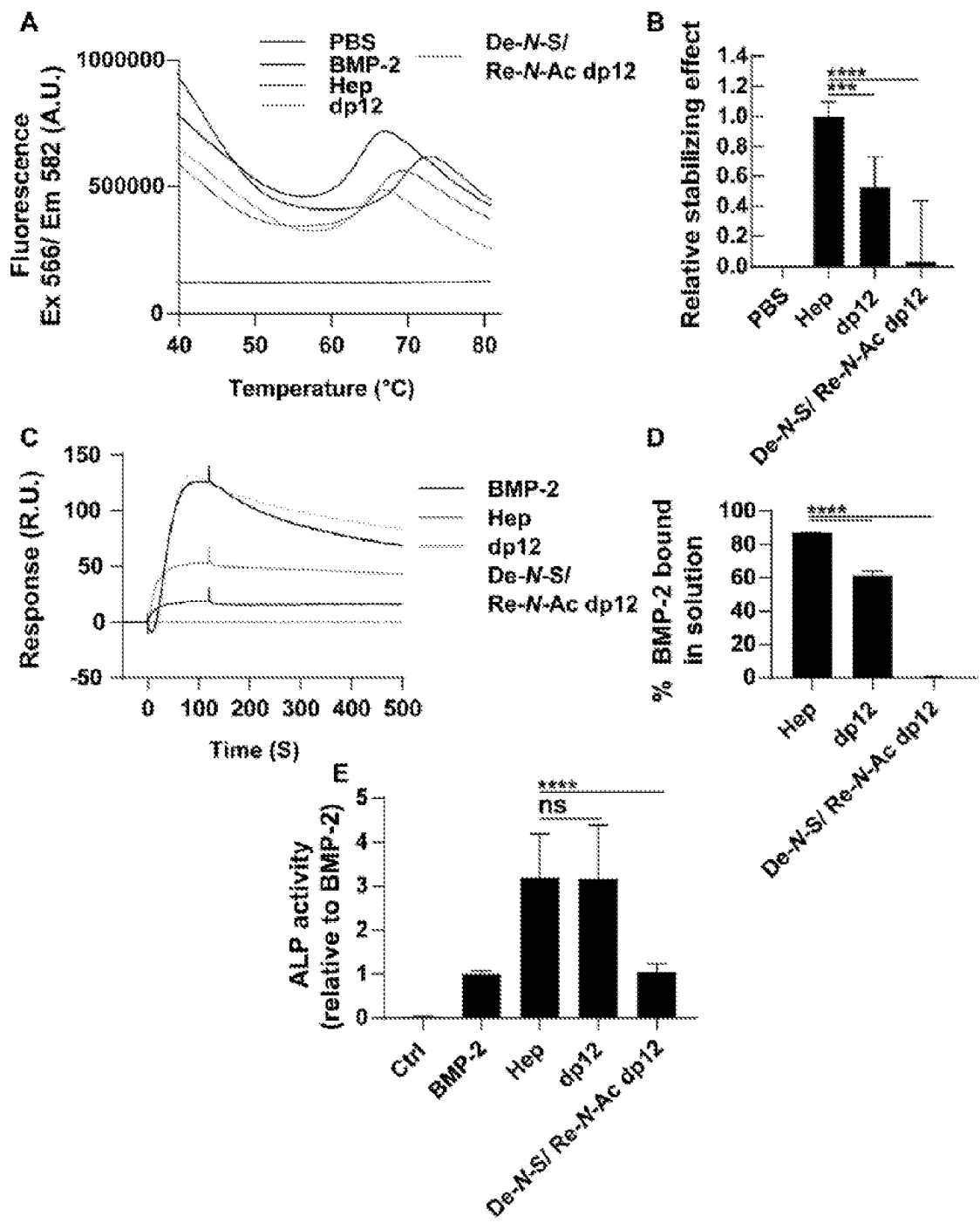
FIG. 12A to 12E. Binding, stabilization and activation of BMP-2 by de-N-sulfated/re-N-acetylated dp12. (A) Representative SPR sensorgrams displaying the binding response generated by heparin, heparin dp12 or de-N-sulfated/re-N-acetylated heparin dp12 (10 μg/mL) pre-incubated with BMP-2 (25 nM) and applied to a heparin-derivitised surface. (B) Normalized SPR data derived from (A) indicating the percentage of BMP-2 sequestered into solution by heparin, heparin dp12 or de-N-sulfated/re-N-acetylated heparin dp12. (C) Differential scanning fluorimetry was performed by incubating BMP-2 (5 μM) in the presence or absence of heparin, heparin dp12 and de-N-sulfated/ re-N-acetylated heparin dp12 (50 μM). (D) Fluorescence generated from the binding of SYPRO orange dye to the core of denatured BMP-2 was used to determine relative complex stability vs. BMP-2+heparin. (E) C2C12 cells were treated with BMP-2 (100 ng/mL) with or without heparin, heparin dp12 or de-N-sulfated/re-N-acetylated heparin dp12 (5 μg/mL) for 3 days, after which protein was extracted and ALP activity was assessed. All data is representative of (A, C) or constitutes mean±S.D. (B, D-E) of three independent experiments. *$p<0.001$, **$p<0.0001$, ns–$p>0.05$.

We next determined the importance of specific sulfate groups within heparin/HS chains BMP-2 binding by using chemically desulfated heparin polysaccharides. A previous study has shown that rat MSCs cultured with de-2-O-sulfated heparin and BMP-2 displayed enhanced MSC proliferation and ALP activity compared to native heparin [38]. Here, N-sulfation proved critical for BMP-2 binding, whilst 6-O-sulfation was less so and 2-O-sulfation had minimal impact on binding. Re—N-acetylation of de-N-sulfated heparin partially rescued BMP-2 binding, but not to the extent of the other desulfated heparin species. Additionally, de-N-sulfated/re-N-acetylated heparin dp12s were incapable of binding BMP-2 and offered little protection from thermal stress, and was unable to enhance BMP-2 bioactivity in vitro, further emphasizing the critical role of N-sulfation in heparin: BMP-2 interactions (FIG. 12). Thus, the contribution of each sulfate group is not equal in the binding of heparin/HS chains to BMP-2, implying that a particular sequence motif underlies this phenomenon. A previous study indicated that a number of variants of desulfated heparin possessed similar net charge but differed significantly in their ability to protect BMP-2 from thermal stress [37]. These data again suggest that sequence and positioning of sulfate groups are essential in the binding of heparin to BMP-2. This result was supported by enhancement of osteogenic gene transcription, ALP activity and mineralization in vitro and the in vivo studies where N-sulfation was crucial for enhancing new bone formation. These results correlate with previous studies showing that N- and 6-O-sulfates are more important than 2-O-sulfates for binding to BMP-7 [17] and BMP-2 [37, 38]. Interestingly, 2-N, 6-O-sulfated chitosan also displayed and ability to enhance BMP-2 biological activity in vitro and in vivo, further indicating the importance of charge placement and density on polysaccharide: BMP-2 interactions [51]. In contrast, the interaction of HS with FGF-1 and FGF-2 require 2-O sulfate groups [31, 46]; although the 6-O sulfate group is less important in binding FGF-2, this substitution plays a critical role in forming the FGF-2-FGF receptor complex, a step essential for FGF-2-mediated signaling [47, 48].

Interestingly, out of all treatment groups we observed the least in vivo bone formation when BMP-2 was complexed with native heparin. This result was unexpected as complexes of BMP-2 and heparin leads to the greatest enhancement of in vitro osteogenesis. Additionally, a previous study by Zhao and colleagues (2006) observed a significant increase in bone formation using identical doses of BMP-2 and heparin, albeit using a different ectopic model [22]. Despite these differences, the observations are comparable to those made in a previous study by our own group using a similar ectopic model with identical doses of BMP-2 and heparin [32]. As eluded to in this previous study, the long-term effects of heparin could differ substantially from the effects seen over shorter periods. Furthermore, a study by Jiao and colleagues (2007) indicated that heparin can have an increasingly inhibitory effect on BMP-2 bioactivity [52]. As previously mentioned, in vivo experiments performed in the study by Ratanavaraporn and Tabata (2012) suggested de-2-O-sulfated heparin enhanced BMP-2-mediated bone formation over native heparin [38]. Moreover, the heparin oligosaccharides and selectively desulfated heparins will possess a more uniform size (in the case of the oligosaccharides) and sulfation pattern (in the case of the desulfated heparins) than native heparin. This increase in homogeneity could result in less off-target or inhibitory effects within the ectopic site. Finally, the heparin oligosaccharides are a lower molecular weight (~2400, 3000 and 3550 Da for dp8, dp10 and dp12 respectively) than native heparin (~15000 Da), decreasing the molar ratio between heparin dp:BMP-2 in the ectopic site and potentially resulting in an increased number of oligosaccharide: BMP-2 interactions, thus enhancing BMP-2-mediated bone formation. This may also explain why we observe a significant increase in ALP activity in C2C12 cells treated with BMP-2+dp12 versus BMP-2+ heparin.

With the knowledge that heparin decasaccharides and de-2-O-sulfated heparin can enhance BMP-2-mediated in vivo bone formation, the rational design of osteoinductive biomaterials may be tuned and enhanced. Indeed, previous studies have noted that de-2-O-sulfation of heparin greatly diminishes the molecules anticoagulant properties [53], which could subsequently lead to fewer off-target effects. Zieris and co-workers (2014) developed a novel starPEG/peptide/heparin hydrogel, using desulfated heparin to sequester growth factors of interest into the biomaterial to enhance cell differentiation [54]. With knowledge of minimum oligosaccharide lengths required for binding of various growth factors and mitogens, such biomaterials could be further tuned to enhance specific interactions between proteins and scaffold, reducing unwanted side effects [55].

Although the details of the mechanism of action of the heparin fragments remain to be elaborated, it has been established that heparin acts to prolong BMP-2-induced cell signaling [22] as evidenced by the phosphorylation of Smad 1/5/9. Here we demonstrated that decasaccharides and N-sulfate groups were necessary to potentiate these effects of BMP-2 in C2C12 cells. Thus, we can conclude that BMP-2 preferences the binding to N-sulfated heparin/HS domains of dp10 or greater over other GAG subtypes. Such confirmatory information is an important step in the rational design and chemical synthesis of HS-based drugs aimed at improving bone tissue repair.

Example 4: Depolymerisation, Sizing and Compositional Analysis of HS-3 and Fragments 4.1. Rationale Data gathered in the heparin oligosaccharide/BMP-2 study (Examples 1-3) defined a minimal structural requirement for the effective stabilization and potentiation of BMP-2's osteoinductive properties in vitro and in vivo:

At least a decamer (dp10; five disaccharides)

NS>6OS>2OS—N-sulfation proved critical for BMP-2 binding, whilst 6-O-sulfation was less so and 2-O-sulfation had minimal impact on binding We therefore hypothesised that HS3 contained a BMP-2 binding region of a certain size and sulphation Due to the fundamental differences in the structure of heparin and HS, we also hypothesised that this will be structurally distinct from a heparin oligosaccharide of equivalent length.

Therefore, we aimed to depolymerise HS3 into pools of oligosaccharides of various size and sulphation in a hope of determining a number of potential structures which may constitute the BMP-2 binding site within HS3.

Heparinase III was used for depolymerisation. Heparinase III cleaves glycosidic linkages between GlcNAc/GlcNS and GlcA residues therefore making it ideal for excising out the highly sulphated domains of HS3.

4.2. Depolymerisation and Sizing

Summary

HS3 was enzymatically cleaved in transition regions (N-acetylated/N-sulfated domains) to liberate the highly charged and active N-sulfated domains. 50 mIU of heparinase III was incubated with 11 mg of HS3 for 24 h, followed by a second 50 mIU addition and 24 h incubation. Digested material was then passed through a 5 kDa molecular weight cut off (MWCO) filter, and the filtrate passed through a 3 kDa MWCO filer. The filtrate and retentate of each filter was then passed over a sephadex G25 column, and material eluting in the column void region (large material) was pooled. Material larger than 5 kDa was then further fractionated by passing through a 10 kDa MWCO filter. Fractions were weighed and re-suspended at 10 mg/mL and stored at −20° C. prior to use.

Depolymerisation Procedure 9 mg HS3 (batch 010), 6 mg HSpm (lot HO-10697) was reconstituted at 10 mg/ml in LC/MS water, and total volume brought up to 900 µL. Then 100 µL 10× heparinise buffer was added. Final salt concentration was 50 mM sodium acetate, 1 mM calcium acetate, pH 7

25 mIU heparinise III was then added to each sample and samples were incubated at 37° C. for 24 h. A second addition of 25 mIU heparinise III was then added to each sample and samples were incubated for further 24 h at 37° C. Digestion was terminated by heating samples to 100° C. for 5 minutes before cooling on ice. Samples were frozen and lyophilised to dryness Initial Sizing Step Procedure Digested HS3 and HSpm were added to pre-washed 5000 Da MWCO Amicon ultra centrifugal filters (4 mL volume) and filtered by centrifuging for 30 minutes at 4000 g. Retentate was kept, filtrate was added to pre-washed 3000

Da MWCO Amicon ultra centrifugal filters (15 mL volume). Samples were filtered by centrifuging for 30 minutes at 4000 g.

Filtrate and retentate were pooled individually into groups: <3 kDa, >3 k-5 Da, and >5 kDa Desalting and Crude Second Sizing Pooled oligosaccharides were desalted and crudely sized using a HiPrep 26/10 desalting column. Superdrex peptide 10/300 gl analytical columns were not used; trial runs resulted in minimal recovery of material, therefore different method was pursued.

Figure 13:
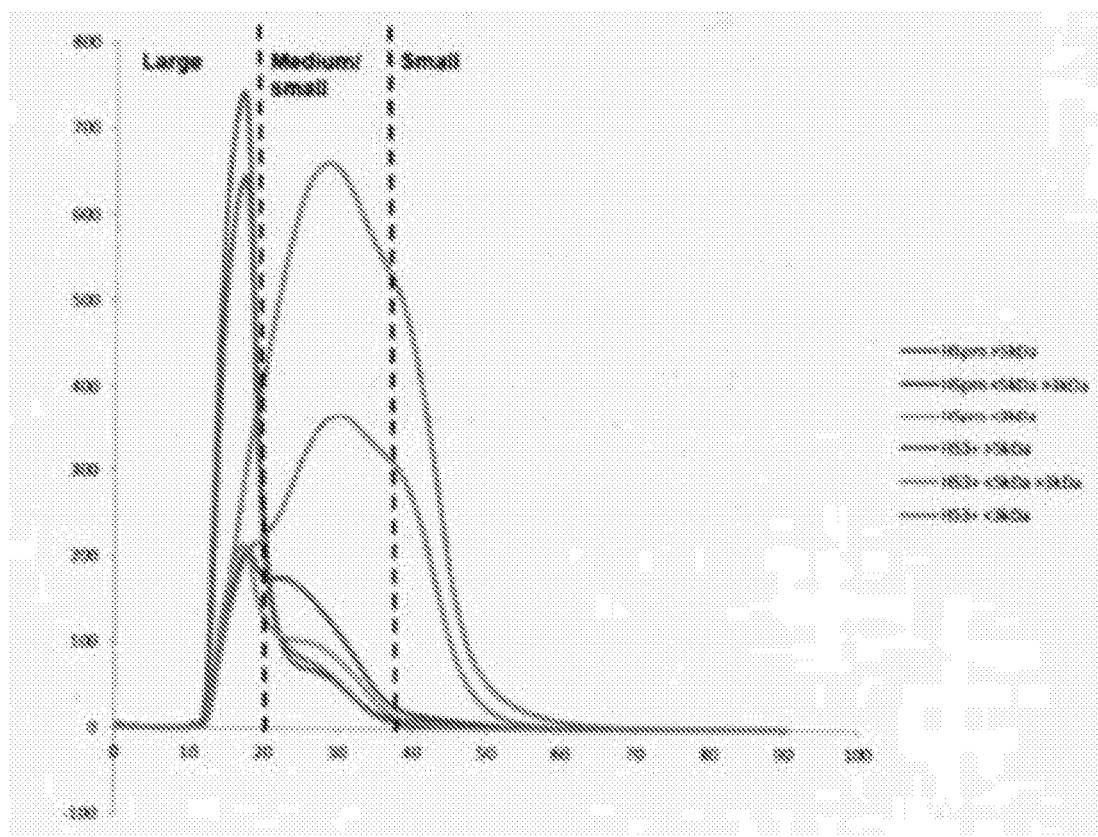
FIG. 13. Graph peaks relate to the crude size groups which were separated and pooled independently.

Samples were loaded in 1 mL total volume followed by 1 mL water. In most cases, a clear peak was observed at the void (FIG. 13), indicating the presence of larger oligosaccharides; there were pooled and further referred to as "large". A broad peak followed, this was pooled as small. In the case of sub-3 kDa material, no sharp peak was observed; instead a much broader peak appeared and crossed into the eluting salt peak. This is consistent with disaccharides. Peaks were pooled, lyophilised and weighed prior to reconstitution in water at 10 mg/mL.

Additional sizing—10 kDa Spin Filter

>5 kDa large HS3 and HSpm were added to pre-washed 10000 Da MWCO Amicon ultra centrifugal filters (0.5 mL volume). Samples were filtered by centrifuging for 30 minutes at 4000 g. Retentate and filtrate were frozen at –80° C. and lyophilised to dryness.

Weights of Sized HS3

HS3>5-10 kDa-1.35 mg

HS3>10 kDa-0.64 mg

Samples were reconstituted at 10 mg/mL in deionised water and stored at –80° C.

4.3. Compositional Analysis of Sized HS3 Fragments

50 μg of each HS3 fragment was digested with 1 mIU of heparinase I, II and III for 24 h at 37° C., followed by an additional 1 mIU of each enzyme and a further 24 h incubation. Digests were terminated by heating to 100° C. for 5 minutes, after which samples were frozen and lyophilised to dryness. Samples were re-suspended in 20 μL 0.1 M 2-aminoacrydone in 85% DMSO/15% acetic acid and incubated for 20 min at room temperature, protected from light. Samples were then reduced overnight with 20 μL 1M sodium cyanoborohydride. After reduction, samples were centrifuged at 13,000 rpm for 10 minutes and the supernatant transferred to a fresh tube. The supernatant was diluted to 400 μL with HPLC-grade water and passed through a 0.22 μm syringe-driven filter. Samples were analysed using a Dionex ICS-3000 high performance liquid chromatography system and resolved using an Agilent Zorbax Eclipse XDB-C18 reverse phase chromatography column. Samples were applied to the column under 95% buffer A (5% buffer B (Acetonitrile) for 1 min, before elution with a gradient of 5%-12% B over 29 min. The column was regenerated with 100% B for 5 min and re-equilibrated with 5% B for 5 min. Samples were detected with an RF2000 fluorescence emission detector (excitation wavelength—425 nm; emission wavelength—520 nm). Disaccharides were identified based on the elution points of known disaccharide standards and peak area corrected using pre-determined correction factors based on variable labelling efficiency between different disaccharide species. Data was normalised as percentage composition and represents three HPLC analysis of an individual digest per sample.

Example 5: HS3 Fragments—Experimental Data 5.1. BMP2 Bioactivity Testing

C2C12 cells were seeded at 20,000 cells/cm2 overnight then treated the following day with the sized heparin fragments, sized HS3 fragments, full length HS3 or full length heparin at 5 μg/mL with 100 ng/mL BMP2 for 72 h. Total protein was extracted, quantified and ALP activity measured and represented as relative ALP activity versus BMP2 alone.

5.2. Enhancement of BMP2-Mediated ALP Activity

Figure 14:
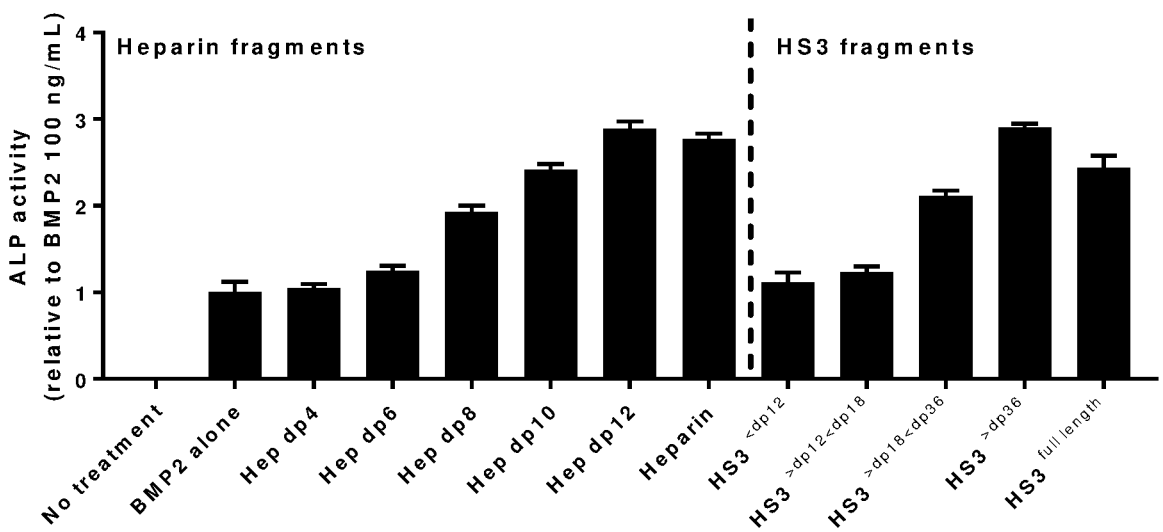
FIG. 14. Relative ALP activity of heparin fragments and HS3 fragments of different lengths.

The data indicates that increasing chain length results in increased ALP activity for both heparin and HS3 oligosaccharides. Unlike heparin fragments, which result in optimal enhancement of BMP2 activity at dp10 and maximal at dp12, HS3 fragments are of at least dp18 and above in length and optimally above dp36 (FIG. 14). This indicates that either the active domains of HS3 are markedly larger, or HS3 requires more than one active domain per chain to enhance BMP2 activity. These data reveal important differences between the two molecules, and suggest that the data generated in the manuscript will not significantly impact on work to elucidate the binding mechanism of HS3 to BMP2.

5.3. Compositional Analysis of HS3 Fragments

Figures 15, 16:
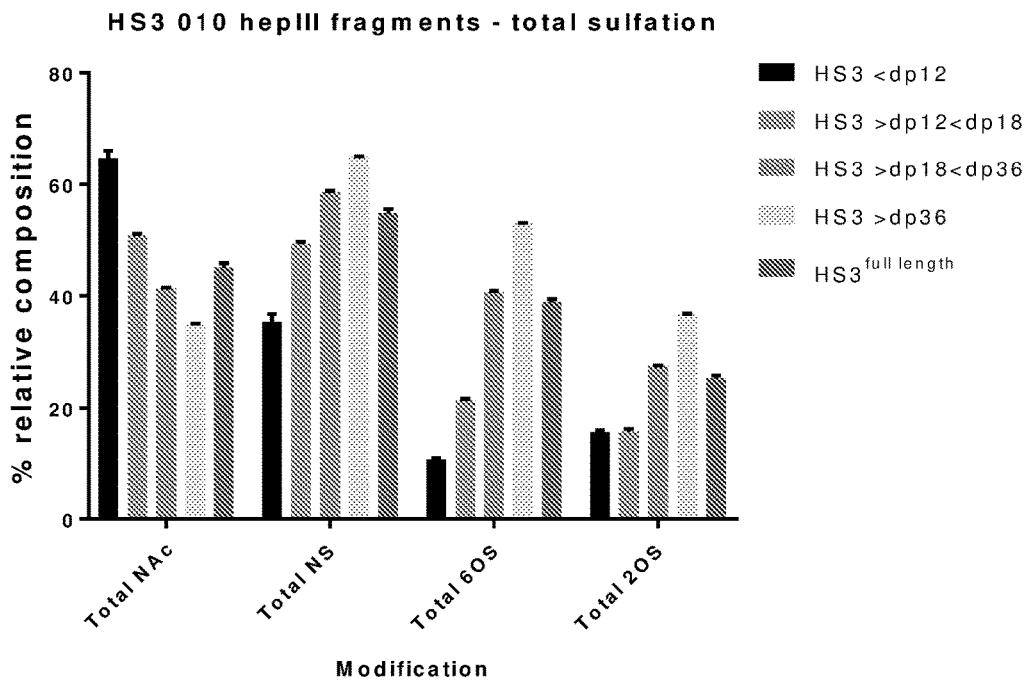
FIG. 15. Sulfation analysis of HS3 fragments. Relative composition of NAc disaccharides, N-sulphated disaccharides, 6-O-sulphated disaccharides and 2-O-sulphated disaccharides in different size HS3 fragments is demonstrated.
FIG. 16. Disaccharide compositional differences between different length HS3 fragments shown in table form.
Figure 17:
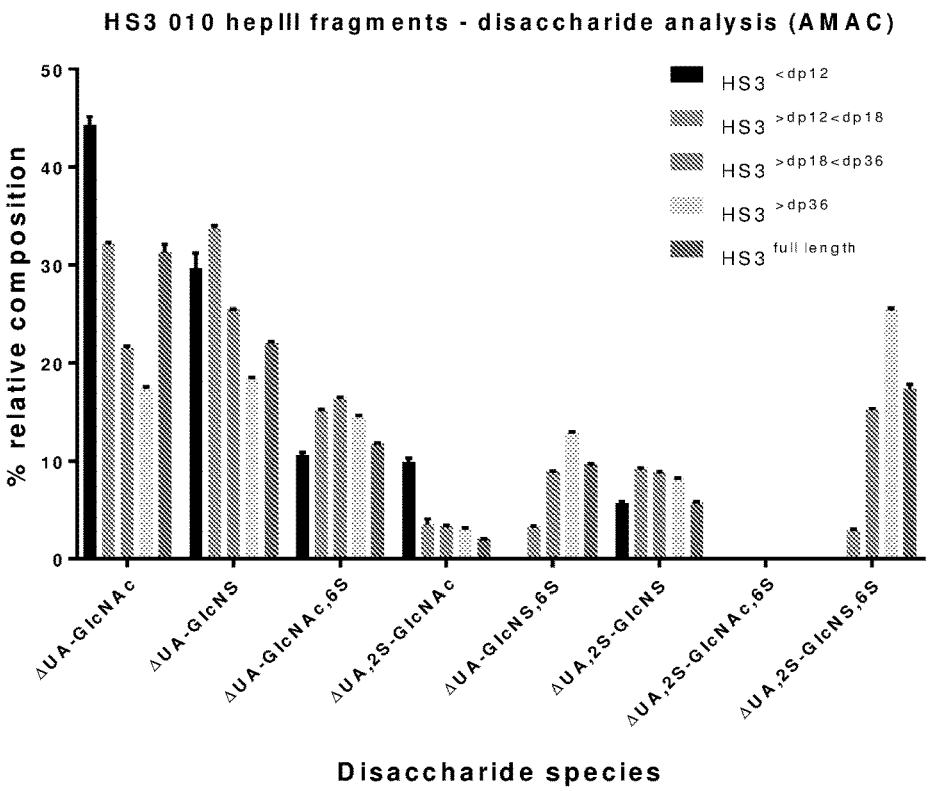
FIG. 17. Disaccharide composition of HS3 fragments with different lengths is demonstrated.

Compositional analysis reveals an obvious trend between length and overall sulphation. The smallest fragments (below a dp12) contain the lowest degree of sulphation (FIG. 15), additionally they possess a greater amount of 2-O-sulphation than 6-O-sulphation, again correlating with data from the manuscript suggesting 6-O-sulphation is more important than 2-O-sulphation in the binding of HS to BMP2. Fragments of 18-36 saccharides display an ability to enhance BMP2-mediated bioactivity, these also contain a higher abundance of sulphation and are compositionally similar to the parental material (HS3 full length, FIGS. 15 and 16). The greatest enhancement of BMP2-mediated bioactivity is induced by fragments above 36 saccharides in length; these are also the most abundantly sulphated species, composed of ~25% trisulphated disaccharides and the highest proportion of N-sulphated, 6-O-sulphated disaccharides (FIGS. 15-17). They also possess the lowest percentage of unmodified disaccharides (table 1, 17.4%). These data suggest that N and 6-O-sulphation are important for the enhancement of BMP2-mediated bioactivity, which correlates with our hypothesis that 2-O-sulphation is the least important modification for enhancing BMP2-mediated bioactivity.

5.4. Compositional Comparisons Between Heparin dp12 and HS3>dp36

Figure 18:
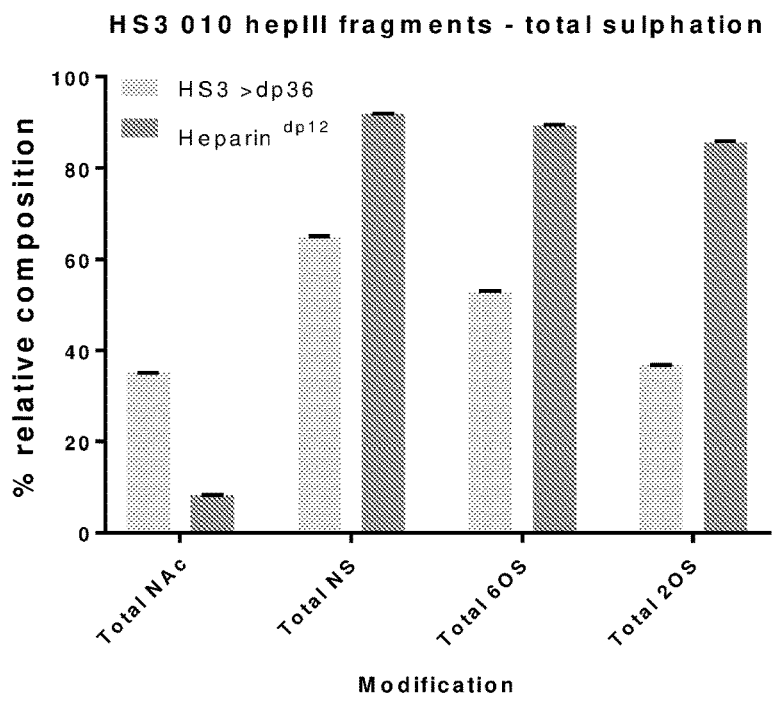
FIG. 18. Sulfation comparisons between heparin dp12 and HS3$^{>dp36}$. Heparin dp12 and HS3$^{>dp36}$ are the most biologically active fragments derived from heparin and HS3. Relative composition of NAc disaccharides, N-sulphated disaccharides, 6-O-sulphated disaccharides and 2-O-sulphated disaccharides in different size HS3 fragments is demonstrated.
Figures 19, 20:
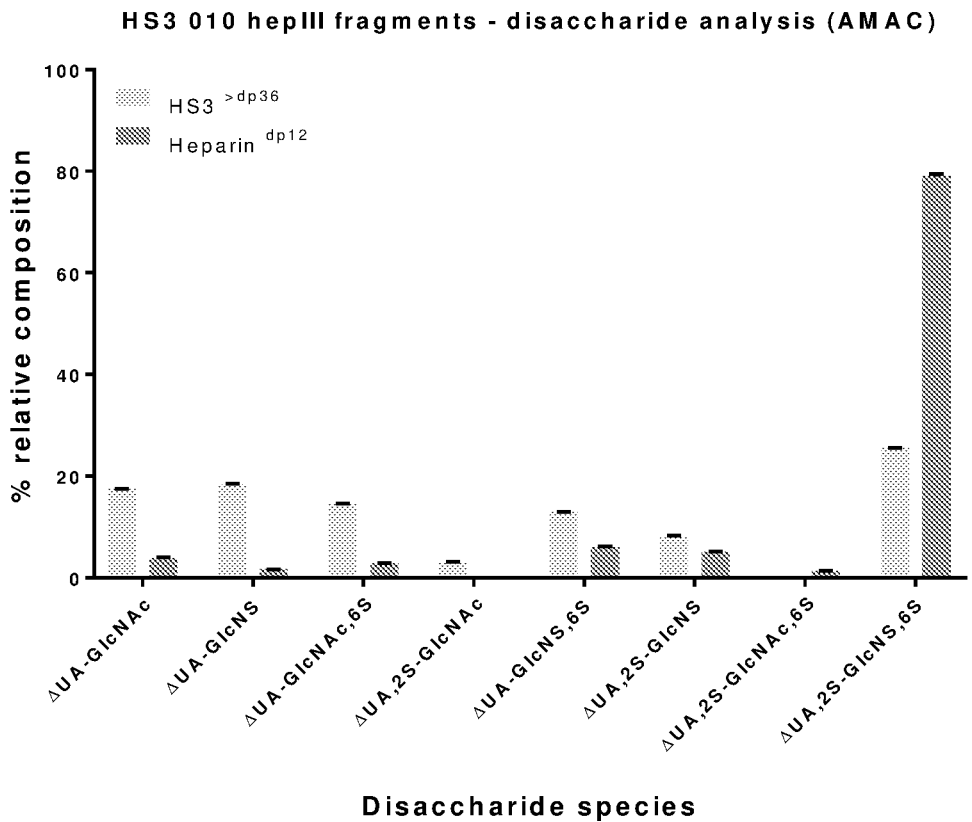
FIG. 19. Disaccharide composition comparison of Heparin dp12 and HS3$^{>dp36}$, the most biologically active fragments derived from heparin and HS3.
FIG. 20. Disaccharide compositional comparisons between heparin dp12 and HS3>dp36. These are the most biologically active fragments of Heparin and HS3 and have different disaccharide compositions and shown in the table.

FIGS. 18, 19 and 20 compare the overall composition of a heparin dp12 and HS3>dp36, which are the most biologically active fragments derived from heparin and HS3, respectively. Structurally, each is distinctly different; the heparin dp12 is predominantly composed of trisulphated residues (Table 2, 79%), whereas the HS3>dp36 contains more mono and disulphated residues with 6-O-sulphation than heparin (14.48% 6-O and 12.97% N—, 6-O vs 2.88% 6-O and 6.03% N—, 6-O, respectively). These data on bioactivity and composition reveal important differences between the two molecules (HS3>dp36 and heparin dp12), and suggest that the data generated in the manuscript will not significantly impact on work to elucidate the binding mechanism of HS3 to BMP2.

REFERENCES

[1] B. L. Hogan, Bone morphogenetic proteins: multifunctional regulators of vertebrate development, Genes Dev 10(13) (1996) 1580-94.

[2] A. H. Reddi, Bone and cartilage differentiation, Curr Opin Genet Dev 4(5) (1994) 737-44.

[3] E. H. Groeneveld, E. H. Burger, Bone morphogenetic proteins in human bone regeneration, Eur J Endocrinol 142(1) (2000) 9-21.

[4] T. J. Kleeman, U. M. Ahn, A. Talbot-Kleeman, Laparoscopic anterior lumbar interbody fusion with rhBMP-2: a prospective study of clinical and radiographic outcomes, Spine (Phila Pa 1976) 26(24) (2001) 2751-6.

[5] J. K. Burkus, E. E. Transfeldt, S. H. Kitchel, R. G. Watkins, R. A. Balderston, Clinical and radiographic outcomes of anterior lumbar interbody fusion using recombinant human bone morphogenetic protein-2, Spine (Phila Pa 1976) 27(21) (2002) 2396-408.

[6] B. McKay, H. S. Sandhu, Use of recombinant human bone morphogenetic protein-2 in spinal fusion applications, Spine (Phila Pa 1976) 27(16 Suppl 1) (2002) S66-85.

[7] A. R. Poynton, J. M. Lane, Safety profile for the clinical use of bone morphogenetic proteins in the spine, Spine (Phila Pa 1976) 27(16 Suppl 1) (2002) S40-8.

[8] K. Miyazono, K. Kusanagi, H. Inoue, Divergence and convergence of TGF-beta/BMP signaling, J Cell Physiol 187(3) (2001) 265-76.

[9] A. Nohe, S. Hassel, M. Ehrlich, F. Neubauer, W. Sebald, Y. I. Henis, P. Knaus, The mode of bone morphogenetic protein (BMP) receptor oligomerization determines different BMP-2 signaling pathways, J Biol Chem 277(7) (2002) 5330-8.

[10] H. Aoki, M. Fujii, T. Imamura, K. Yagi, K. Takehara, M. Kato, K. Miyazono, Synergistic effects of different bone morphogenetic protein type I receptors on alkaline phosphatase induction, J Cell Sci 114(Pt 8) (2001) 1483-9.

[11] J. Massague, Y. G. Chen, Controlling TGF-beta signaling, Genes Dev 14(6) (2000) 627-44.

[12] L. Attisano, J. L. Wrana, Smads as transcriptional co-modulators, Curr Opin Cell Biol 12(2) (2000) 235-43.

[13] A. H. Reddi, Bone morphogenetic proteins: from basic science to clinical applications, J Bone Joint Surg Am 83-A Suppl 1(Pt 1) (2001) S1-6.

[14] T. Katagiri, N. Takahashi, Regulatory mechanisms of osteoblast and osteoclast differentiation, Oral Dis 8(3) (2002) 147-59.

[15] E. Forsberg, L. Kjellen, Heparan sulfate: lessons from knockout mice, J Clin Invest 108(2) (2001) 175-80.

[16] S. Grisaru, D. Cano-Gauci, J. Tee, J. Filmus, N. D. Rosenblum, Glypican-3 modulates BMP- and FGF-mediated effects during renal branching morphogenesis, Dev Biol 231(1) (2001) 31-46.

[17] A. Irie, H. Habuchi, K. Kimata, Y. Sanai, Heparan sulfate is required for bone morphogenetic protein-7 signaling, Biochem Biophys Res Commun 308(4) (2003) 858-65.

[18] S. Paine-Saunders, B. L. Viviano, A. N. Economides, S. Saunders, Heparan sulfate proteoglycans retain Noggin at the cell surface: a potential mechanism for shaping bone morphogenetic protein gradients, J Biol Chem 277(3) (2002) 2089-96.

[19] S. Paine-Saunders, B. L. Viviano, J. Zupicich, W. C. Skarnes, S. Saunders, glypican-3 controls cellular responses to Bmp4 in limb patterning and skeletal development, Dev Biol 225(1) (2000) 179-87.

[20] T. Takada, T. Katagiri, M. Ifuku, N. Morimura, M. Kobayashi, K. Hasegawa, A. Ogamo, R. Kamijo, Sulfated polysaccharides enhance the biological activities of bone morphogenetic proteins, J Biol Chem 278(44) (2003) 43229-35.

[21] T. Katagiri, A. Yamaguchi, M. Komaki, E. Abe, N. Takahashi, T. Ikeda, V. Rosen, J. M. Wozney, A. Fujisawa-Sehara, T. Suda, Bone morphogenetic protein-2 converts the differentiation pathway of C2C12 myoblasts into the osteoblast lineage, J Cell Biol 127(6 Pt 1) (1994) 1755-66.

[22] B. Zhao, T. Katagiri, H. Toyoda, T. Takada, T. Yanai, T. Fukuda, U. I. Chung, T. Koike, K. Takaoka, R. Kamijo, Heparin potentiates the in vivo ectopic bone formation induced by bone morphogenetic protein-2, J Biol Chem 281(32) (2006) 23246-53.

[23] D. A. Pye, J. T. Gallagher, Monomer complexes of basic fibroblast growth factor and heparan sulfate oligosaccharides are the minimal functional unit for cell activation, J Biol Chem 274(19) (1999) 13456-61.

[24] M. Lyon, G. Rushton, J. A. Askari, M. J. Humphries, J. T. Gallagher, Elucidation of the structural features of heparan sulfate important for interaction with the Hep-2 domain of fibronectin, J Biol Chem 275(7) (2000) 4599-606.

[25] O. Ostrovsky, B. Berman, J. Gallagher, B. Mulloy, D. G. Fernig, M. Delehedde, D. Ron, Differential effects of heparin saccharides on the formation of specific fibroblast growth factor (FGF) and FGF receptor complexes, J Biol Chem 277(4) (2002) 2444-53.

[26] I. Capila, R. J. Linhardt, Heparin-protein interactions, Angew Chem Int Ed Engl 41(3) (2002) 391-412.

[27] D. Loganathan, H. M. Wang, L. M. Mallis, R. J. Linhardt, Structural variation in the antithrombin III binding site region and its occurrence in heparin from different sources, Biochemistry 29(18) (1990) 4362-8.

[28] J. Choay, M. Petitou, J. C. Lormeau, P. Sinay, B. Casu, G. Gatti, Structure-activity relationship in heparin: a synthetic pentasaccharide with high affinity for antithrombin III and eliciting high anti-factor Xa activity, Biochem Biophys Res Commun 116(2) (1983) 492-9.

[29] S. T. Olson, I. Bjork, R. Sheffer, P. A. Craig, J. D. Shore, J. Choay, Role of the antithrombin-binding pentasaccharide in heparin acceleration of antithrombin-proteinase reactions. Resolution of the antithrombin conformational change contribution to heparin rate enhancement, J Biol Chem 267(18) (1992) 12528-38.

[30] U. Lindahl, G. Backstrom, M. Hook, L. Thunberg, L. A. Fransson, A. Linker, Structure of the antithrombin-binding site in heparin, Proc Natl Acad Sci USA 76(7) (1979) 3198-202.

[31] J. E. Turnbull, D. G. Fernig, Y. Ke, M. C. Wilkinson, J. T. Gallagher, Identification of the basic fibroblast growth factor binding sequence in fibroblast heparan sulfate, J Biol Chem 267(15) (1992) 10337-41.

[32] D. S. Bramono, S. Murali, B. Rai, L. Ling, W. T. Poh, Z. X. Lim, G. S. Stein, V. Nurcombe, A. J. van Wijnen, S. M. Cool, Bone marrow-derived heparan sulfate potentiates the osteogenic activity of bone morphogenetic protein-2 (BMP-2), Bone 50(4) (2012) 954-64.

[33] R. A. A. Smith, R. J. E. Chua, S. M. Carnachan, C. L. L. Tan, I. M. Sims, S. F. R. Hinkley, V. Nurcombe, S. M. Cool, Retention of the Structure and Function of Heparan Sulfate Biomaterials After Gamma Irradiation, Tissue Eng Part A 24(9-10) (2018) 729-739.

[34] S. Murali, B. Rai, C. Dombrowski, J. L. Lee, Z. X. Lim, D. S. Bramono, L. Ling, T. Bell, S. Hinkley, S. S. Nathan, J. H. Hui, H. K. Wong, V. Nurcombe, S. M. Cool, Affinity-selected heparan sulfate for bone repair, Biomaterials 34(22) (2013) 5594-605.

[35] B. Rai, J. L. Lin, Z. X. Lim, R. E. Guldberg, D. W. Hutmacher, S. M. Cool, Differences between in vitro viability and differentiation and in vivo bone-forming

[36] J. Lee, S. Wee, J. Gunaratne, R. J. Chua, R. A. Smith, L. Ling, D. G. Fernig, K. Swaminathan, V. Nurcombe, S. M. Cool, Structural determinants of heparin-transforming growth factor-beta1 interactions and their effects on signaling, Glycobiology 25(12) (2015) 1491-504.

[37] S. P. Seto, T. Miller, J. S. Temenoff, Effect of selective heparin desulfation on preservation of bone morphogenetic protein-2 bioactivity after thermal stress, Bioconjug Chem 26(2) (2015) 286-93.

[38] J. Ratanavaraporn, Y. Tabata, Enhanced osteogenic activity of bone morphogenetic protein-2 by 2-O-desulfated heparin, Acta biomaterialia 8(1) (2012) 173-82.

[39] P. C. Tyler, S. E. Guimond, J. E. Turnbull, O. V. Zubkova, Single-entity heparan sulfate glycomimetic clusters for therapeutic applications, Angew Chem Int Ed Engl 54(9) (2015) 2718-23.

[40] R. Schworer, O. V. Zubkova, J. E. Turnbull, P. C. Tyler, Synthesis of a targeted library of heparan sulfate hexa- to dodecasaccharides as inhibitors of beta-secretase: potential therapeutics for Alzheimer's disease, Chemistry 19(21) (2013) 6817-23.

[41] S. S. Deepa, Y. Umehara, S. Higashiyama, N. Itoh, K. Sugahara, Specific molecular interactions of oversulfated chondroitin sulfate E with various heparin-binding growth factors. Implications as a physiological binding partner in the brain and other tissues, J Biol Chem 277(46) (2002) 43707-16.

[42] U. Lindahl, G. Backstrom, L. Thunberg, I. G. Leder, Evidence for a 3-O-sulfated D-glucosamine residue in the antithrombin-binding sequence of heparin, Biochemistry 77(11) (1980) 6551-6555.

[43] U. Lindahl, L. Thunberg, G. Backstrom, J. Riesenfeld, K. Nordling, I. Bjork, Extension and structural variability of the antithrombin-binding sequence in heparin, J Biol Chem 259(20) (1984) 12368-76.

[44] L. Thunberg, G. Backstrom, U. Lindahl, Further characterization of the antithrombin-binding sequence in heparin, Carbohydr Res 100 (1982) 393-410.

[45] C. J. Robinson, N. J. Harmer, S. J. Goodger, T. L. Blundell, J. T. Gallagher, Cooperative dimerization of fibroblast growth factor 1 (FGF1) upon a single heparin saccharide may drive the formation of 2:2:1 FGF1.FGFR2c.heparin ternary complexes, J Biol Chem 280(51) (2005) 42274-82.

[46] M. Guerrini, T. Agulles, A. Bisio, M. Hricovini, L. Lay, A. Naggi, L. Poletti, L. Sturiale, G. Torri, B. Casu, Minimal heparin/heparan sulfate sequences for binding to fibroblast growth factor-1, Biochem Biophys Res Commun 292(1) (2002) 222-30.

[47] D. A. Pye, R. R. Vives, P. Hyde, J. T. Gallagher, Regulation of FGF-1 mitogenic activity by heparan sulfate oligosaccharides is dependent on specific structural features: differential requirements for the modulation of FGF-1 and FGF-2, Glycobiology 10(11) (2000) 1183-92.

[48] S. Guimond, M. Maccarana, B. B. Olwin, U. Lindahl, A. C. Rapraeger, Activating and inhibitory heparin sequences for FGF-2 (basic FGF). Distinct requirements for FGF-1, FGF-2, and FGF-4, J Biol Chem 268(32) (1993) 23906-14.

[49] K. A. Radek, K. R. Taylor, R. L. Gallo, FGF-10 and specific structural elements of dermatan sulfate size and sulfation promote maximal keratinocyte migration and cellular proliferation, Wound Repair Regen 17(1) (2009) 118-26.

[50] K. R. Taylor, J. A. Rudisill, R. L. Gallo, Structural and sequence motifs in dermatan sulfate for promoting fibroblast growth factor-2 (FGF-2) and FGF-7 activity, J Biol Chem 280(7) (2005) 5300-6.

[51] H. Zhou, J. Qian, J. Wang, W. Yao, C. Liu, J. Chen, X. Cao, Enhanced bioactivity of bone morphogenetic protein-2 with low dose of 2-N, 6-O-sulfated chitosan in vitro and in vivo, Biomaterials 30(9) (2009) 1715-24.

[52] X. Jiao, P. C. Billings, M. P. O'Connell, F. S. Kaplan, E. M. Shore, D. L. Glaser, Heparan sulfate proteoglycans (HSPGs) modulate BMP2 osteogenic bioactivity in C2C12 cells, J Biol Chem 282(2) (2007) 1080-6.

[53] U. Freudenberg, A. Zieris, K. Chwalek, M. V. Tsurkan, M. F. Maitz, P. Atallah, K. R. Levental, S. A. Eming, C. Werner, Heparin desulfation modulates VEGF release and angiogenesis in diabetic wounds, J Control Release 220 (Pt A) (2015) 79-88.

[54] A. Zieris, R. Dockhorn, A. Rohrich, R. Zimmermann, M. Muller, P. B. Welzel, M. V. Tsurkan, J. U. Sommer, U. Freudenberg, C. Werner, Biohybrid networks of selectively desulfated glycosaminoglycans for tunable growth factor delivery, Biomacromolecules 15(12) (2014) 4439-46.

[55] U. Freudenberg, Y. Liang, K. L. Kiick, C. Werner, Glycosaminoglycan-Based Biohybrid Hydrogels: A Sweet and Smart Choice for Multifunctional Biomaterials, Adv Mater 28(40) (2016) 8861-8891.

[56] D. Xu, J. D. Esko, Demystifying Heparan Sulfate-Protein Interactions, Annual review of biochemistry 83 (2014) 129-157.

[57] A. Ori, M. C. Wilkinson, D. G. Fernig, A systems biology approach for the investigation of the heparin/heparan sulfate interactome, J Biol Chem 286(22) (2011) 19892-904.

[58] B. I. Ayerst, R. A. Smith, V. Nurcombe, A. J. Day, C. L. Merry, S. M. Cool, Growth Differentiation Factor 5-Mediated Enhancement of Chondrocyte Phenotype Is Inhibited by Heparin: Implications for the Use of Heparin in the Clinic and in Tissue Engineering Applications, Tissue Eng Part A 23(7-8) (2017) 275-292.

[59] A. Walker, J. E. Turnbull, J. T. Gallagher, Specific heparan sulfate saccharides mediate the activity of basic fibroblast growth factor, J Biol Chem 269(2) (1994) 931-5.

[60] J. Kreuger, K. Prydz, R. F. Pettersson, U. Lindahl, M. Salmivirta, Characterization of fibroblast growth factor 1 binding heparan sulfate domain, Glycobiology 9(7) (1999) 723-729.

[61] J. Kreuger, M. Salmivirta, L. Sturiale, G. Gimenez-Gallego, U. Lindahl, Sequence analysis of heparan sulfate epitopes with graded affinities for fibroblast growth factors 1 and 2, The Journal of Biological Chemistry 276(33) (2001) 30744-52.

[62] D. Spillmann, D. Witt, U. Lindahl, Defining the Interleukin-8-binding Domain of Heparan Sulfate, The Journal of Biological Chemistry 273(25) (1998) 15487-15493.

[63] N. S. Gandhi, R. L. Mancera, Prediction of heparin binding sites in bone morphogenetic proteins (BMPs), Biochim Biophys Acta 1824(12) (2012) 1374-81.

[64] B. Rai, A. Chatterjea, Z. X. Lim, T. C. Tan, A. A. Sawyer, Y. Z. Hosaka, S. Murali, J. J. Lee, S. A. Fenwick, J. H. Hui, V. Nurcombe, S. M. Cool, Repair of segmental ulna defects using a beta-TCP implant in combination with a heparan sulfate glycosaminoglycan variant, Acta biomaterialia 28 (2015) 193-204.

[65] K. A. Uniewicz, A. Ori, R. Xu, Y. Ahmed, M. C. Wilkinson, D. G. Fernig, E. A. Yates, Differential Scanning Fluorimetry Measurement of Protein Stability Changes upon Binding to Glycosaminoglycans: A Screening Test for Binding Specificity, Anal Chem 82(9) (2010) 3796-3802.
[66] H. S. Yang, W. G. La, S. H. Bhang, J. Y. Jeon, J. H. Lee, B. S. Kim, Heparin-conjugated fibrin as an injectable system for sustained delivery of bone morphogenetic protein-2, Tissue Eng Part A 16(4) (2010) 1225-33.
[67] Z. A. Ralis, and Watkins, K., Modified tetrachrome method for osteoid and defectively mineralized bone in paraffin sections, Biotech and Histochem 67(6) (1992) 339-345.

The invention claimed is:

1. A method of treatment, the method comprising the step of administering an isolated heparin or heparan sulphate oligosaccharide to a subject in need thereof,
wherein the method also comprises:
a method of wound healing in vivo,
the repair and/or regeneration of connective tissue,
the repair and/or regeneration of bone,
the repair and/or regeneration of bone in a mammal or a human, or
the repair and/or regeneration of a broken bone,
and wherein the isolated heparin or heparan sulphate oligosaccharide:
has a chain length of at least 12 saccharides and no more than 50 saccharides; and
is capable of binding BMP2.

2. The method of claim 1, wherein the isolated heparin or heparan sulphate oligosaccharide has a chain length of about 12 saccharides.

3. The method of claim 1, wherein the isolated heparin or heparan sulphate enhances BMP2-mediated ALP activity.

4. The method of claim 3, wherein the isolated heparin or heparan sulphate enhances BMP2-mediated ALP activity as measured in an in vitro assay of BMP2-mediated ALP activity.

5. The method of claim 1, wherein the isolated heparin or heparan sulphate enhances BMP2-mediated Smad 1/5/9 phosphorylation.

6. The method of claim 5, wherein the isolated heparin or heparan sulphate enhances BMP2-mediated Smad 1/5/9 phosphorylation as measured in an in vitro assay of BMP2-mediated Smad 1/5/9 phosphorylation.

7. The method of claim 1, wherein the isolated heparin or heparan sulphate is N-sulphated.

8. The method of claim 1, wherein the isolated heparin or heparan sulphate is 6-0 sulphated.

9. The method of claim 1, wherein the isolated heparin or heparan sulphate is 2-0 de-sulphated.

10. The method of claim 1, wherein the isolated heparin or heparan sulphate is a fragment of HS3.

11. The method of claim 1, wherein the isolated heparin or heparan sulphate oligosaccharide has a chain length of 14 to 50 saccharides, 16 to 50 saccharides, 18 to 50 saccharides, 20 to 50 saccharides, 22 to 50 saccharides, 24 to 50 saccharides, 26 to 50 saccharides, 28 to 50 saccharides, 30 to 50 saccharides, 32 to 50 saccharides, 34 to 50 saccharides, 36 to 50 saccharides, 38 to 50 saccharides, 40 to 50 saccharides, 42 to 50 saccharides, 44 to 50 saccharides, 46 to 50 saccharides, or 48 to 50 saccharides.

12. The method of claim 1, wherein the isolated heparin or heparan sulphate oligosaccharide has a chain length of 12 to 36 saccharides, 14 to 36 saccharides, 16 to 36 saccharides, 18 to 36 saccharides, 20 to 36 saccharides, 22 to 36 saccharides, 24 to 36 saccharides, 26 to 36 saccharides, 28 to 36 saccharides, 30 to 36 saccharides, 32 to 36 saccharides, or 34 to 36 saccharides.

13. The method of claim 1, wherein the isolated heparin or heparan sulphate oligosaccharide has a chain length of 36 to 50 saccharides, 38 to 50 saccharides, 40 to 50 saccharides, 42 to 50 saccharides, 44 to 50 saccharides, 46 to 50 saccharides, or 48 to 50 saccharides.

14. The method of claim 1, wherein the isolated heparin or heparan sulphate oligosaccharide has a chain length of 18 to 40 saccharides, 20 to 40 saccharides, 22 to 40 saccharides, 24 to 40 saccharides, 26 to 40 saccharides, 28 to 40 saccharides, 30 to 40 saccharides, 32 to 40 saccharides, 34 to 40 saccharides, 36 to 40 saccharides, or 38 to 40 saccharides.

15. A method of treating a bone fracture in a patient, the method comprising surgically implanting a biocompatible implant or prosthesis, which comprises a biomaterial and an isolated heparin or heparan sulphate into tissue of the patient at or surrounding the site of fracture;
  wherein the isolated heparin or heparan sulphate oligosaccharide:
    has a chain length of at least 12 saccharides and no more than 50 saccharides; and
    is capable of binding BMP2.

16. The method of claim 15, wherein the isolated heparin or heparan sulphate oligosaccharide has a chain length of 14 to 50 saccharides, 16 to 50 saccharides, 18 to 50 saccharides, 20 to 50 saccharides, 22 to 50 saccharides, 24 to 50 saccharides, 26 to 50 saccharides, 28 to 50 saccharides, 30 to 50 saccharides, 32 to 50 saccharides, 34 to 50 saccharides, 36 to 50 saccharides, 38 to 50 saccharides, 40 to 50 saccharides, 42 to 50 saccharides, 44 to 50 saccharides, 46 to 50 saccharides, or 48 to 50 saccharides.

17. The method of claim 15, wherein the isolated heparin or heparan sulphate oligosaccharide has a chain length of 12 to 36 saccharides, 14 to 36 saccharides, 16 to 36 saccharides, 18 to 36 saccharides, 20 to 36 saccharides, 22 to 36 saccharides, 24 to 36 saccharides, 26 to 36 saccharides, 28 to 36 saccharides, 30 to 36 saccharides, 32 to 36 saccharides, or 34 to 36 saccharides.

18. The method of claim 15, wherein the isolated heparin or heparan sulphate oligosaccharide has a chain length of 36 to 50 saccharides, 38 to 50 saccharides, 40 to 50 saccharides, 42 to 50 saccharides, 44 to 50 saccharides, 46 to 50 saccharides, or 48 to 50 saccharides.

19. The method of claim 15, wherein the isolated heparin or heparan sulphate oligosaccharide has a chain length of 18 to 40 saccharides, 20 to 40 saccharides, 22 to 40 saccharides, 24 to 40 saccharides, 26 to 40 saccharides, 28 to 40 saccharides, 30 to 40 saccharides, 32 to 40 saccharides, 34 to 40 saccharides, 36 to 40 saccharides, or 38 to 40 saccharides.

20. The method of claim 15, wherein the isolated heparin or heparan sulphate oligosaccharide is a fragment of HS3.

21. The method of claim 1, wherein the repair and/or regeneration of bone is the repair of a bone fracture.

22. The method of claim 1, wherein the repair and/or regeneration of bone is the repair and/or regeneration of a long bone. short bone, flat bone, irregular bone, and/or sesamoid bone.

23. The method of claim 1, wherein the repair and/or regeneration of bone is the repair and/or regeneration of a bone of the cranio-facial region, a bone of the face, a bone of the mouth, jaw and/or vertebrae.

24. The method of claim 1, wherein the isolated heparin or heparan sulphate oligosaccharide is administered during dental, facial, or cranial surgery.

25. The method of claim 1, wherein the isolated heparin or heparan sulphate oligosaccharide is administered as a biomaterial that is coated and/or impregnated with isolated heparin or heparan sulphate.

26. The method of claim 25, wherein the biomaterial is a hydrogel, fibrin, collagen, ceramic, metal, an autograft, or an allograft biomaterial.

\* \* \* \* \*